(12) United States Patent
Melton et al.

(10) Patent No.: US 11,262,348 B2
(45) Date of Patent: Mar. 1, 2022

(54) CELL-BASED ASSAYS FOR DETECTION OF ANTIBODIES OR OTHER FACTORS THAT NEUTRALIZE UPTAKE OF LYSOSOMAL ENZYMES

(71) Applicant: BIOMARIN PHARMACEUTICAL INC., Novato, CA (US)

(72) Inventors: Andrew Melton, Novato, CA (US); Stephen Zoog, Novato, CA (US); Lynne Jesaitis, Novato, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 582 days.

(21) Appl. No.: 15/773,822

(22) PCT Filed: Nov. 7, 2016

(86) PCT No.: PCT/US2016/060795
§ 371 (c)(1),
(2) Date: May 4, 2018

(87) PCT Pub. No.: WO2017/079729
PCT Pub. Date: May 11, 2017

(65) Prior Publication Data
US 2018/0321221 A1  Nov. 8, 2018

Related U.S. Application Data

(60) Provisional application No. 62/252,181, filed on Nov. 6, 2015.

(51) Int. Cl.
*G01N 33/573* (2006.01)
*G01N 33/50* (2006.01)
(Continued)

(52) U.S. Cl.
CPC ..... *G01N 33/5008* (2013.01); *G01N 33/5005* (2013.01); *G01N 33/573* (2013.01);
(Continued)

(58) Field of Classification Search
None
See application file for complete search history.

(56) References Cited

U.S. PATENT DOCUMENTS

| 4,391,904 A | 7/1983 | Litman et al. |
| 7,485,314 B2 | 2/2009 | Kakkis et al. |

(Continued)

FOREIGN PATENT DOCUMENTS

| CN | 102027110 A | 4/2011 |
| CN | 103797115 A | 5/2014 |

(Continued)

OTHER PUBLICATIONS

Ao et al., FluoroImmunoassay for antigen based on fluorescence quenching signal of gold nanoparticles, Anal. Chem., 78(4):1104-6 (2006).

(Continued)

*Primary Examiner* — Rebecca M Giere
(74) *Attorney, Agent, or Firm* — Marshall, Gerstein & Borun LLP

(57) ABSTRACT

The present invention relates to cell-based methods for screening body fluids or tissues for factors that prevent cellular uptake of lysosomal enzymes, including neutralizing factors such as neutralizing antibodies, that arise as a result of lysosomal enzyme replacement therapy.

23 Claims, 15 Drawing Sheets

(51) Int. Cl.

| | |
|---|---|
| C12N 5/0783 | (2010.01) |
| G01N 33/49 | (2006.01) |
| G01N 33/533 | (2006.01) |
| G01N 33/543 | (2006.01) |
| G01N 33/68 | (2006.01) |

(52) U.S. Cl.
CPC ........ *C12N 5/0636* (2013.01); *G01N 33/4915* (2013.01); *G01N 33/533* (2013.01); *G01N 33/5434* (2013.01); *G01N 33/6854* (2013.01)

(56) References Cited

U.S. PATENT DOCUMENTS

| | | | |
|---|---|---|---|
| 7,713,709 B2 | 5/2010 | White et al. | |
| 7,785,856 B2 | 8/2010 | LeBowitz et al. | |
| 8,563,691 B2 | 10/2013 | LeBowitz et al. | |
| 8,859,498 B2 | 10/2014 | LeBowitz et al. | |
| 9,044,473 B2 | 6/2015 | Kakkis | |
| 9,089,566 B2 | 7/2015 | Kakkis | |
| 2008/0003626 A1* | 1/2008 | White ................ | G01N 33/6854 435/7.92 |
| 2014/0161788 A1 | 6/2014 | Aoyagi-Scharber et al. | |

FOREIGN PATENT DOCUMENTS

| | | |
|---|---|---|
| CN | 104160033 A | 11/2014 |
| WO | WO-2007/109155 A2 | 9/2007 |
| WO | WO-2011/000958 A1 | 1/2011 |

OTHER PUBLICATIONS

Banugaria et al., The impact of antibodies on clinical outcomes in diseases treated with therapeutic protein: lessons learned from infantile Pompe disease, Genet. Med., 13(8):729-36 (2011).

Barbier et al., The relationship between anti-idursulfase antibody status and safety and efficacy outcomes in attenuated mucopolysaccharidosis II patients aged 5 years and older treated with intravenous idursulfase, Mol. Genet. Metab., 110(3):303-10 (2013).

Bayer et al., The avidin-biotin complex in affinity cytochemistry, Methods Enzymol., 62:308-15 (1979).

Brands et al., Mucopolysaccharidosis type VI phenotypes-genotypes and antibody response to galsulfase, Orphanet. J. Rare Dis., 8:51 (2013).

Brooks et al., Significance of immune response to enzyme-replacement therapy for patients with a lysosomal storage disorder, Trends Mol. Biol., 9(10):450-3 (2003).

Bénichou et al., A retrospective analysis of the potential impact of IgG antibodies to agalsidase beta on efficacy during enzyme replacement therapy for Fabry disease, Mol. Genet. Metab., 96(1):4-12 (2009).

Desnick et al., Enzyme replacement therapy for lysosomal diseases: lessons from 20 years of experience and remaining challenges, Annu. Rev. Genomics Hum. Genet., 13:307-35 (2012).

Dvorak-Ewell et al., Enzyme replacement in a human model of mucopolysaccharidosis IVA in vitro and its biodistribution in the cartilage of wild type mice, PLoS One, 5(8):e12194 (2010).

Engvall et al., Enzyme-linked immunosorbent assay, Elisa. 3. Quantitation of specific antibodies by enzyme-labeled anti-immunoglobulin in antigen-coated tubes, J. Immunol., 109(1):129-35 (1972).

Fineberg et al., Immunologic effects of insulin lispro [Lys (B28), Pro (B29) human insulin] in IDDM and NIDDM patients previously treated with insulin, Diabetes, 45(12):1750-4 (1996).

Goding, Conjugation of antibodies with fluorochromes: modifications to the standard methods, J. Immunol. Methods, 13(3-4):215-26 (1976).

Graham et al., Characteristics of a human cell line transformed by DNA from human adenovirus type 5, J. Gen. Virol., 36(1):59-74 (1977).

Gupta et al., Recommendations for the design, optimization, and qualification of cell-based assays used for the detection of neutralizing antibody responses elicited to biological therapeutics, J. Immunol. Methods, 321(1-2):1-18 (2007).

Guss et al., Structure of the IgG-binding regions of streptococcal protein G, EMBO J., 5(7):1567-75 (1986).

Harmatz, Enzyme Replacement Therapies and Immunogenicity in Lysosomal Storage Diseases: Is There a Pattern?, Clin. Ther., 37(9):2130-4 (2015).

Hendriksz et al., Efficacy and safety of enzyme replacement therapy with BMN 110 (elosulfase alfa) for Morquio A syndrome (mucopolysaccharidosis IVA): a phase 3 randomised placebo-conliolled study, J. Inherit. Metab. Dis., 37(6):979-90 (2014).

Hendriksz et al., Impact of long-term elosulfase alfa treatment on respiratory function in patients with Morquio A syndrome, J. Inherit. Metab. Dis., 39(6):839-47 (2016).

International Application No. PCT/US2016/060795, International Preliminary Report on Patentability, dated May 8, 2018.

International Application No. PCT/US2016/060795, International Search Report and Written Opinion, dated Jan. 2, 2017.

Jameson et al., Enzyme replacement therapy with laronidase (Aldurazyme) for treating mucopolysaccharidosis type I, Cochrane Database Syst. Rev., (9):CD009354 (2013).

Kakkis et al., Enzyme-replacement therapy in mucopolysaccharidosis I, N. Engl. J. Med., 344(3):182-8 (2001).

Kakkis, Enzyme replacement therapy for the mucopolysaccharide storage disorders, Expert Opin. Investig. Drugs, 11(5):675-85 (2002).

Kishnani et al., Cross-reactive immunologic material status affects treatment outcomes in Pompe disease infants, Mol. Genet. Metab., 99(1):26-33 (2010).

Lindmark et al., Binding of immunoglobulins to protein A and immunoglobulin levels in mammalian sera, J. Immunol. Methods, 62(1):1-13 (1983).

Liu et al., Solid-substrate room-temperature phosphorescence immunoassay based on an antibody labeled with nanoparticles containing dibromofluorescein luminescent molecules and analytical application, J. Immunol. Methods, 307:34-40 (2005).

Long et al., Long-term Immunogenicity of Elosulfase Alfa in the Treatment of Morquio A Syndrome: Results From MOR-005, a Phase III Extension Study, Clin. Ther., 39(1):118-129.e3 (2017).

Marnell et al., A Chinese hamster ovary cell mutant with a heat-sensitive, conditional-lethal defect in vacuolar function, J. Cell Biol., 99(6):1907-16 (1984).

Mather et al., Culture of testicular cells in hormone-supplemented serum-free medium, Ann. N Y Acad. Sci., 383:44-68 (1982).

Mather, Establishment and characterization of two distinct mouse testicular epithelial cell lines, Biol. Reprod., 23(1):243-52 (1980).

Melton et al., Antibodies that neutralize cellular uptake of elosulfase alfa are not associated with reduced efficacy or pharmacodynamic effect in individuals with Morquio A syndrome, J. Immunol. Methods, 440:41-51 (2017).

Melton, A Cell-Based Flow Cytometry Assay to Detect and Titer Neutralizing Antibodies that Block Uptake of Enzyme Replacement Therapies Utilizing CI-M6PR, Poster Abstract, presented on Nov. 18, 2015 at the Advances in Bioassay Technologies sub-section at the 2015 Cambridge Healthtech Institute (CHI) Immunogenicity and Bioassay Summit, held Nov. 17-19 in Baltimore, MD.

Millonig et al., High-dose intravenous interferon beta in patients with neutralizing antibodies (HINABS): a pilot study, Mult. Scler., 15(8):977-83 (2009).

Mire-Sluis et al., Recommendations for the design and optimization of immunoassays used in the detection of host antibodies against biotechnology products, J. Immunol. Methods, 289(1-2):1-16 (2004).

Motyka et al., Mannose 6-phosphate/insulin-like growth factor II receptor is a death receptor for granzyme B during cytotoxic T cell-induced apoptosis, Cell, 103(3):491-500 (2000).

Muenzer, Mucopolysaccharidoses, Adv. Pediatr., 33:269-302 (1986).

Munier-Lehmann et al., Function of the two mannose 6-phosphate receptors In lysosomal enzyme transport, Biochem. Soc. Trans., 24(1):133-6 (1996).

Osman et al., Evidence for an association between the T cell receptor/CD3 antigen complex and the CD5 antigen in human T lymphocytes, Eur. J. Immunol., 22(11):2995-3000 (1992).

(56) References Cited

OTHER PUBLICATIONS

Oyama et al., Catalytic residues and substrate specificity of recombinant human tripeptidyl peptidase I (CLN2), J. Biochem., 138(2):127-34 (2005).

Qi et al., Pharmacokinetic and pharmacodynamic evaluation of elosulfase alfa, an enzyme replacement therapy in patients with Morquio A syndrome, Clin. Pharmacokinet., 53(12):1137-47 (2014).

Sahlin et al., Differentiation between attached and ingested immune complexes by a fluorescence quenching cytofluorometric assay, J. Immunol. Methods, 60(1-2):115-24 (1983).

Schweighardt et al., Immunogenicity of Elosulfase Alfa, an Enzyme Replacement Therapy in Patients With Morquio A Syndrome: Results From MOR-004, a Phase III Trial, Clin. Ther., 37(5):1012-21.e6 (2015).

Shankar et al., Recommendations for the validation of immunoassays used for detection of host antibodies against biotechnology products, J. Pharm. Biomed. Anal., 48(5):1267-81 (2008).

Soon et al., A cell-based flow cytometry assay to detect and titer neutralizing antibodies that block uptake of enzyme replacement therapies utilizing CI-M6PR, poster session presented on Nov. 18, 2015 at the Advances in Bioassay Technologies sub-section at the 2015 Cambridge Healthtech Institute (CHI) Immunogenicity and Bioassay Summit, held Nov. 17-19 in Baltimore, MD.

Starr et al., Fluorophore-assisted electrophoresis of urinary carbohydrates for the identification of patients with oligosaccharidosis- and mucopolysaccharidosis-type lysosomal storage diseases, Glycosylation & Disease, 1(3):165-76 (1994).

Sternberger et al., The unlabeled antibody enzyme method of immunohistochemistry: preparation and properties of soluble antigen-antibody complex (horseradish peroxidase-antihorseradish peroxidase) and its use in identification of spirochetes, J. Histochem. Cytochem., 18(5):315-33 (1970).

Séllos-Moura et al., Development of a panel of highly sensitive, equivalent assays for detection of antibody responses to velaglucerase alfa or imiglucerase enzyme replacement therapy in patients with Gaucher disease, J. Immunol. Methods, 373(1-2):45-53 (2011).

Urlaub et al., Isolation of Chinese hamster cell mutants deficient in dihydrofolate reductase activity, Proc. Natl. Acad. Sci. USA, 77(7):4216-20 (1980).

Van Gelder et al., Antibody formation to enzyme therapy in classic infantile Pompe disease: implications of patient age, BMC Musculoskeletal Dis., 14(Suppl 2): P18 (2013).

Walkley et al., GM2 ganglioside as a regulator of pyramidal neuron dendritogenesis, Ann. N Y Acad. Sci., 845:188-99 (1998).

Wang et al., Neutralizing antibodies to therapeutic enzymes: considerations for testing, prevention and treatment, Nat. Biotechnol., 26(8):901-8 (2008).

Wood et al., Cell surface-expressed cation-independent mannose 6-phosphate receptor (CD222) binds enzymatically active heparanase independently of mannose 6-phosphate to promote extracellular matrix degradation, J. Biol. Chem., 283(7):4165-76 (2008).

Vachvanichsanong et al., Childhood idiopathic hypercalciuria. Int. Pediatr., 9(1):40-8 (1994).

Zhou et al., Glycan structure determinants for cation-independent mannose 6-phosphate receptor binding and cellular uptake of a recombinant protein, Bioconjug. Chem., 21(12):2025-35 (2013).

* cited by examiner

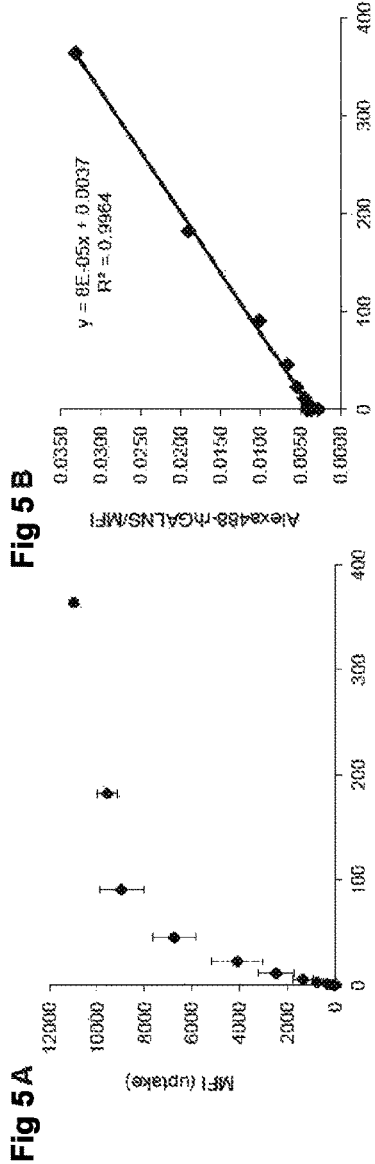
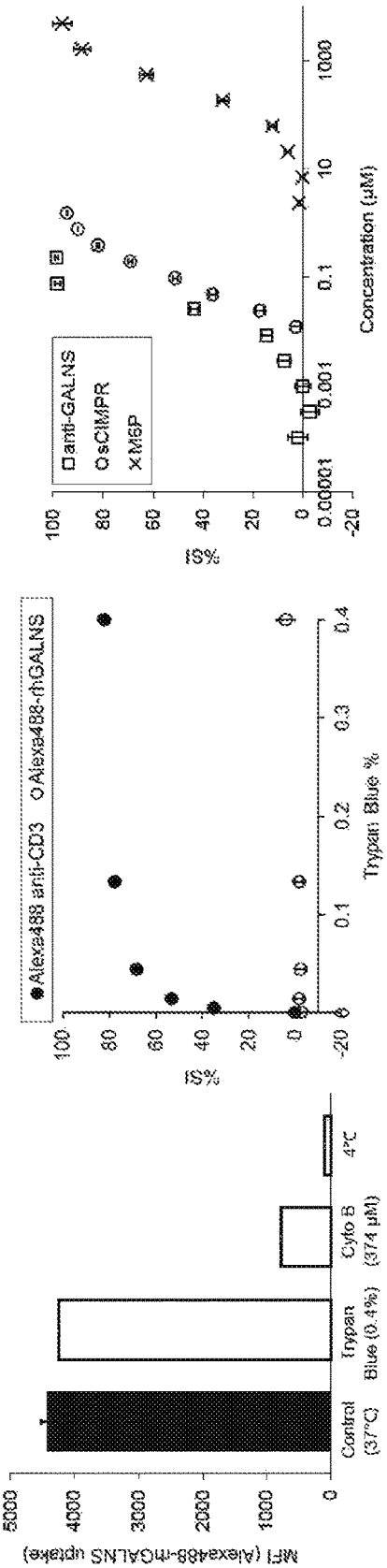

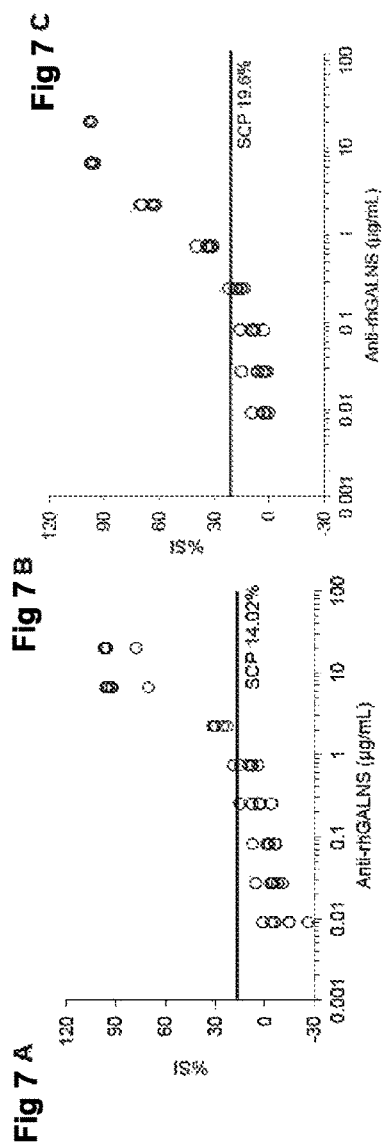

Fig 10

| Treatment Group | Study Week | Receptor Binding (-) Cellular Uptake (-) | Receptor Binding (+) Cellular Uptake (+) | Receptor Binding (-) Cellular Uptake (+) | Receptor Binding (+) Cellular Uptake (-) |
|---|---|---|---|---|---|
| Placebo | Baseline | 59(100.0) | | | |
| | 2 | 59(100.0) | | | |
| | 4 | 58(100.0) | | | |
| | 8 | 57(100.0) | | | |
| | 12 | 56(94.9) | 1(1.7) | | 2(3.4) |
| | 16 | 57(96.6) | | | 2(3.4) |
| | 20 | 58(98.3) | | | 1(1.7) |
| | 24 | 57(96.6) | | | 2(3.4) |
| 2.0 mg/kg/QOW | Baseline | 59(100.0) | | | |
| | 2 | 54(93.1) | 1(1.7) | | 3(5.2) |
| | 4 | 47(79.7) | 7(11.9) | | 5(8.5) |
| | 8 | 14(23.7) | 40(67.8) | 3(5.1) | 2(3.4) |
| | 12 | 7(12.1) | 43(74.1) | 3(5.2) | 5(8.6) |
| | 16 | 9(15.5) | 42(72.4) | | 7(12.1) |
| | 20 | 5(8.5) | 44(74.6) | 3(5.1) | 7(11.9) |
| | 24 | 8(14.0) | 41(71.9) | 2(3.5) | 6(10.5) |

| 2.0 mg/kg/QW | | | | |
|---|---|---|---|---|
| Baseline | 57(98.3) | | | |
| 2 | 45(80.4) | | 1(1.7) | 3(5.4) |
| 4 | 12(21.4) | 4(7.1) | 4(7.1) | 4(7.1) |
| 8 | 2(3.6) | 39(69.6) | 1(1.8) | 3(5.5) |
| 12 | 3(5.6) | 47(85.5) | 3(5.5) | |
| 16 | 2(3.6) | 47(87.0) | 4(7.4) | 5(8.9) |
| 20 | 3(5.3) | 49(87.5) | 1(1.8) | 7(12.3) |
| 24 | 6(11.1) | 46(80.7) | 1(1.9) | 4(7.4) |
| | | 43(79.6) | | |

Fig 10 continued

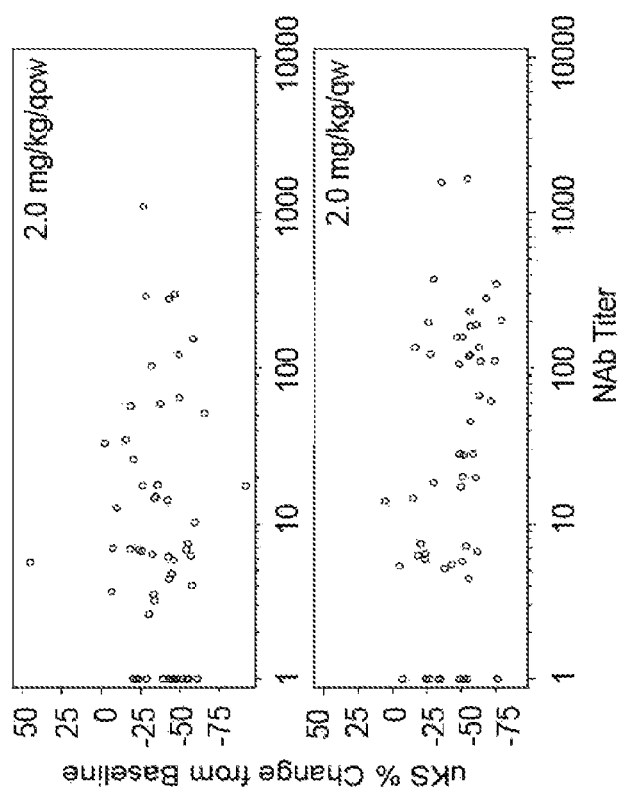
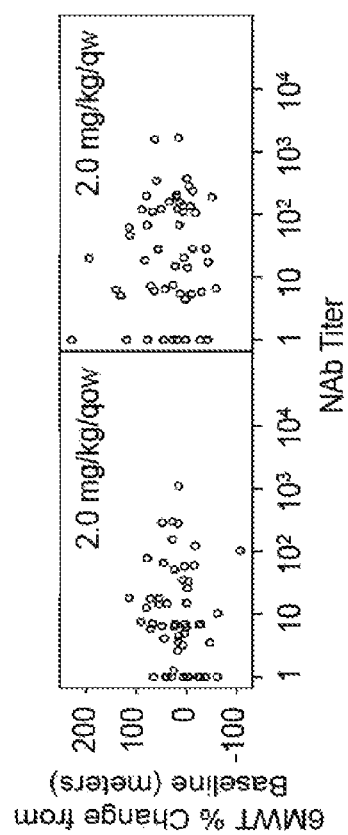
Fig 11 B
Fig 11 A

CELL-BASED ASSAYS FOR DETECTION OF ANTIBODIES OR OTHER FACTORS THAT NEUTRALIZE UPTAKE OF LYSOSOMAL ENZYMES

CROSS-REFERENCE TO RELATED APPLICATIONS

This application is a National Stage Application of International Patent Application No. PCT/US2016/060795, filed Nov. 7, 2018, which claims the priority benefit from U.S. Provisional Patent Application No. 62/252,181, filed Nov. 6, 2015, which is incorporated by reference in its entirety.

FIELD OF THE INVENTION

The present invention relates to cell-based methods for screening body fluids or tissues for factors that neutralize cellular uptake of lysosomal enzymes administered as part of enzyme replacement therapy.

BACKGROUND OF THE INVENTION

Lysosomal storage diseases, including mucopolysaccharidoses (MPS) (Klock et al., Internat Pediatr. 9:40-48 (1994); Starr et al., Glycosylation & Disease 1:165-176 (1994)), are caused by a deficiency in an enzyme or combination of enzymes. These lysosomal storage diseases are often characterized by intralysosomal accumulation of undegraded glycosaminoglycans, or "storage material," excessive urinary excretion of glycosaminoglycans, progressive mental and physical deterioration, and premature death. Patients are usually born without the visible clinical features of lysosomal storage disorders, but develop progressive clinical involvement. Each type of storage disorder has specific lysosomal enzyme deficiency with a characteristic degree of organ involvement and rate of deterioration. See Muenzer, Adv. Pediatri. 33:269-302 (1986). A large number of lysosomal enzymes have been identified and correlated with their related diseases. Once a missing enzyme has been identified, treatment can be reduced to the sole problem of efficiently delivering a replacement enzyme to the affected tissues of patients.

Some patients die from disease-related complications between childhood and early adulthood. One way to treat lysosomal storage diseases is by intravenous enzyme replacement therapy (ERT) (Kakkis, Expert Opin Investig Drugs 11(5):675-85 (2002)). ERT takes advantage of the vasculature to carry enzyme from a single site of administration to most tissues. Once the enzyme has been widely distributed, it must be taken up into cells. The basis for uptake into cells is found in a unique feature of lysosomal enzymes: lysosomal enzymes constitute a separate class of glycoproteins defined by phosphate at the 6-position of terminal mannose residues. Mannose 6-phosphate is bound with high affinity and specificity by a receptor found on the surface of most cells (Munier-Lehmann et al., Biochem. Soc. Trans. 24(1): 133-6 (1996); Marnell et al., J. Cell. Biol. 99(6):1907-16 (1984)). The cation-independent mannose 6-phosphate receptor (CI-MPR) directs uptake of enzyme from blood to tissue and then mediates intracellular routing to the lysosome. Another related mechanism for lysosomal delivery involves a glycosylation independent lysosomal targeting peptide (GILT) that exploits a distinct binding region of the same CI-MPR molecule to facilitate uptake. See e.g., U.S. Pat. Nos. 8,859,498 and 8,563,691, herein incorporated by reference.

A potential side effect of administration of enzyme replacement therapy (ERT) is the development of enzyme-specific antibodies or other neutralizing factors in patients receiving multiple rounds of therapy. These enzyme-specific antibodies or other factors may precipitate potential adverse events and changes in clinical efficacy, changes in pharmacokinetic profile, neutralization of the enzymatic activity, interference with receptor-mediated enzyme uptake, and breaking of tolerance toward self-proteins.

For example, a number of ERTs for the treatment of various lysosomal storage disorders, including elosulfase alfa, contain mannose-6-phosphate (M6P) moieties and depend on the CI-M6PR transmembrane receptor for internalization and trafficking to the lysosome. Biological therapies can elicit an immune response, resulting in the generation of antidrug antibodies capable of binding to the drug product and, in some cases, interfering with receptor binding on the target cell. Furthermore, these antibodies may negatively impact efficacy [Brooks et al., Trends Mol.Med. 9 (2003) 450-453; Desnick et al., Annu. Rev. Genomics Hum. Genet. 13 (2012) 307-335; Banugaria et al., Genet. Med. 13 (2011) 729-736]. A clinical study showed that all individuals treated with elosulfase alfa developed drug-specific total antibodies (TAb). A subset of drug-specific antibodies may be elosulfase alfa-specific neutralizing antibodies (NAbs) capable of interfering with CI-M6PR binding, positivity for which was revealed using an ELISA-based in vitro assay (CI-M6PR binding assay). Although elosulfase alfa-specific antibody development was universal among treated individuals in the clinical study, no relationship was detected between TAb titers or NAb positivity and the magnitude of physical improvements or reductions in uKS levels [Schweighardt et al., Clin.Ther. 37 (2015) 1012-1021.e6].

Reliable assays to accurately measure development of anti-enzyme neutralizing factors would enable assessment of the treatment regimen in a patient receiving ERT and facilitate more efficient design of patient therapy (Mire-Sluis et al., J. Immunological Methods 289:1-16 (2004)).

SUMMARY OF INVENTION

The present disclosure is based on the development of specific and cell-based selective assays for the measurement of neutralizing factors, such as antibodies, that develop in association with protein therapeutics, including enzyme replacement therapy, for lysosomal storage disorders. The disclosure describes a novel, cell-based flow cytometry method for identifying and titering NAbs capable of inhibiting cellular uptake (functional NAb assay) to determine if this measurement might be more clinically meaningful than measuring inhibition of receptor binding, as was measured in previous studies.

One aspect of the invention is a method for detecting lysosomal enzyme (LE)-specific neutralizing factors in a subject (e.g., a human) comprising the steps of: (a) contacting a body fluid sample from the subject with a lysosomal enzyme conjugated to a detection moiety to detect LE-specific neutralizing factors in the body fluid sample, wherein the LE-specific neutralizing factor and lysosomal enzyme detection moiety form a complex; (b) contacting the LE-specific factor/lysosomal enzyme detection moiety complex from step (a) with cells comprising a cation independent mannose-6-phosphate receptor (CI-MPR); and (c) detecting the presence of LE-specific neutralizing factor in the body fluid sample by detecting the presence of the lysosomal enzyme labeled with the detection moiety inside the cell or on the surface of the cell.

Also provided is a method for determining the presence of lysosomal enzyme (LE)-specific neutralizing factors in a subject comprising the steps of: (a) contacting a body fluid sample from the subject with a lysosomal enzyme conjugated to a detection moiety to detect LE-specific neutralizing factors in the body fluid sample, wherein the LE-specific neutralizing factor and lysosomal enzyme detection moiety form a complex; (b) contacting the LE-specific neutralizing factor/lysosomal enzyme detection moiety complex from step (a) with cells comprising a cation independent mannose-6-phosphate receptor (CI-MPR); and (c) detecting the presence of LE-specific neutralizing factor from the body fluid sample by detecting the lysosomal enzyme labeled with the detection moiety inside the cell or on the surface of the cell, wherein a low amount of detectable LE-detection moiety is indicative of the presence of LE-specific neutralizing factors in the sample.

In various embodiments, the body fluid sample and lysosomal enzyme-detection moiety are contacted together in the same solution prior to contacting with cells.

In various embodiments, the body fluid sample, lysosomal enzyme-detection moiety and cells are contacted together in the same solution, for example, wherein the contacting begins simultaneously.

The disclosure also provides a method for determining the percent inhibition of lysosomal enzyme activity by lysosomal enzyme (LE)-specific neutralizing factors in a subject comprising the steps of: (a) contacting a body fluid sample from the subject with LE-conjugated magnetic beads; (b) contacting the body fluid sample/LE-bead combination from step (a) with a composition comprising a lysosomal enzyme conjugated to a detection moiety to detect LE-specific neutralizing factors in the body fluid sample; (c) contacting the combination of (a) and (b) with cells comprising a cation independent mannose-6-phosphate receptor (CI-MPR), and (d) detecting the presence of LE-specific neutralizing factor in the body fluid sample from the combination of (a), (b) and (c) and comparing the levels of LE-specific neutralizing factor to a control sample with a known amount of LE-specific neutralizing antibody in order to determine the percent inhibition of LE activity by neutralizing factors in the body fluid sample.

In various embodiments, the levels of LE-specific neutralizing factor in the body fluid sample are determined by detecting the presence of the lysosomal enzyme labeled with the detection moiety inside the cell or on the surface of the cell.

In various embodiments, a reduced level of detection in the presence of the body fluid sample compared to control indicates that the body fluid sample contains a neutralizing factor that inhibits LE uptake.

In various embodiments, the body fluid sample, lysosomal enzyme-bead conjugate and lysosomal enzyme-detection moiety conjugate are contacted together in the same solution prior to contacting with cells.

In various embodiments, the body fluid sample, lysosomal enzyme-bead conjugate, lysosomal enzyme-detection moiety conjugate and cells are all contacted together in the same solution, for example, wherein the contacting begins simultaneously.

In various embodiments, the body fluid sample and lysosomal enzyme-detection moiety conjugate are contacted together for at least about 6 hours prior to contacting with cells.

In various embodiments, the body fluid sample, lysosomal enzyme-bead conjugate and lysosomal enzyme-detection moiety conjugate are contacted together for at least about 6 hours prior to contacting with cells. In various embodiments, the contacting takes place for at least about 6, 7, 8, 9, 10, 11 or 12 hours.

In various embodiments, the body fluid sample is contacted with the LE-detection moiety conjugate for at least about six hours. In various embodiments, the contacting can be for at least about 6, 7, 8, 9, 10, 11 or 12 hours. In various embodiments, the body fluid sample and LE-detection moiety are contacted for at least about six hours at approximately 4° C.

In various embodiments, the body fluid sample, lysosomal enzyme-bead conjugate and lysosomal enzyme-detection moiety are contacted with the cells for about three hours. In various embodiments, the body fluid sample and lysosomal enzyme-detection moiety are contacted with the cells for about three hours. In various embodiments, the samples are contacted with the cells for at least three hours at approximately 37° C. In various embodiments, the contacting with cells can be for about 3, 4, 5 or 6 hours. In various embodiments, the contacting with cells is for about 3, 3.25, 3.5, 3.75 or 4 hours.

In various embodiments, the molar concentration of the lysosomal enzyme-detection moiety conjugate is about the same or less than the molar concentration of the lysosomal enzyme-bead conjugate. In various embodiments, the lysosomal enzyme-bead conjugate and lysosomal enzyme-detection moiety conjugate are used in about equimolar ratios.

In various embodiments, the detecting is by flow cytometry.

In various embodiments, the cells are cells that naturally or recombinantly express the CI-MPR. In various embodiments, the cells are T cells, including Jurkat T cells, macrophages, HepG2 cells, HeLa cells, MCF-7 cells, NIH3T3 cells and peripheral blood mononuclear cells (PBMCs).

In various embodiments, the limit of detection is less than about 500 ng/mL, or less than about 100 ng/mL. In various embodiments, the limit of detection is less than or equal to about 45 µg/mL.

In various embodiments, the limit of detection is about 1.7 ng/mL to about 8.5 ng/mL.

In various embodiments, LE-specific neutralizing factors in a subject can be detected from a species selected from the group consisting of human, cynomolgus monkey, feline, canine, rabbit, goat, rat and mouse. In various embodiments, the species is human. In various embodiments, the LE-specific neutralizing factor is a neutralizing antibody and the species is human.

In various embodiments, the body fluid is selected from the group consisting of blood, urine, cerebrospinal fluid, plasma and serum. In various embodiments, the body fluid is serum. In various embodiments, body fluid samples are collected just prior to weekly or every other week dosing of therapeutic enzyme.

In various embodiments, the lysosomal enzyme is selected from the group consisting of N-acetylgalactosamine 6-sulfatase (rhGALNS), N-acetyl-glucosaminidase (Naglu), tripeptidyl peptidase 1 (TPP1) and acid alpha glucosidase (GAA).

In various embodiments, the enzyme is taken up by the CI-MPR via mannose 6 phosphate or via an IGF-II GILT tag.

In various embodiments, the neutralizing factor is selected from the group consisting of a neutralizing antibody, mannose 6 phosphate, IGF-II, an IGF-II peptide, IGF-II peptide analogs and soluble CI-MPR. In various embodiments, the neutralizing factor is a neutralizing antibody.

In various embodiments, the neutralizing factor is a neutralizing antibody and the detection moiety is a fluorophore.

In various embodiments, the detection moiety is a fluorophore. Exemplary fluorophores contemplated for use in the method include, but are not limited to, Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, phycoerythrin (PE), fluorescein isothiocyanate (FITC), BODIPY FL, BODIPY 630/650, Cy2, Cy3, Cy3B, Cy3.5, Cy5, Cy5.5, Cy7, ECD, FITC, FluorX®, Cascade® Blue, Pacific Blue®, Pacific Green®, Pacific Orange®, eFluor® 450, eFluor® 605NC, eFluor® 625NC, eFluor® 650NC, eFluor® 660, eFluor® 710, Brilliant Violet™ (BV) fluorophores BV421, BV510, BV570, BV 605, BV650, BD Horizon™ V450, BD Horizon™ V500, Texas Red, rhodamine, cyanine, phycocyanin, allophycocyanin (APC), o-phthaldehyde, fluorescamine, Oregon Green® 488, PE-APC, PE-Cy5, PerCP, PE-TR, rhodamine green and rhodol green, and tandem dyes thereof.

In various embodiments, a first washing step is performed after step (a) and a second washing step is performed after step (b). In various embodiments, the method optionally comprises a washing step performed after step (c).

Also contemplated is a method for treating a patient with a lysosomal storage disease and undergoing enzyme replacement therapy comprising measuring levels of LE-neutralizing factors in a sample from the patient using methods described herein, and if neutralizing factors are detected that interfere with efficacy of the ERT, then administering to the patient an immunosuppressive therapy, and/or reducing the amount of enzyme administered during enzyme replacement therapy.

For example, provided herein is a method for treating a subject having a lysosomal storage disease and receiving enzyme replacement therapy comprising (a) contacting a body fluid sample from the subject with a lysosomal enzyme conjugated to a detection moiety to detect LE-specific neutralizing factors in the body fluid sample, wherein the LE-specific neutralizing factor and lysosomal enzyme detection moiety form a complex; (b) contacting the LE-specific factor/lysosomal enzyme detection moiety complex from step (a) with cells comprising a cation independent mannose-6-phosphate receptor (CI-MPR); (c) detecting the presence of LE-specific neutralizing factor in the body fluid sample by detecting the presence of the lysosomal enzyme labeled with the detection moiety inside the cell or on the surface of the cell, (d) determining whether the LE-specific neutralizing factors interfere with efficacy of the enzyme replacement therapy, and (e) altering the therapy regimen when the LE-specific neutralizing factors interfere with efficacy of the enzyme replacement therapy, optionally wherein the subject is further administered an immunosuppressive drug and/or the dose of enzyme replacement therapy for the subject is reduced.

Also provided herein is a method for treating a subject having a lysosomal storage disease and receiving enzyme replacement therapy comprising (a) contacting a body fluid sample from the subject with a lysosomal enzyme conjugated to a detection moiety to detect LE-specific neutralizing factors in the body fluid sample, wherein the LE-specific neutralizing factor and lysosomal enzyme detection moiety form a complex; (b) contacting the LE-specific neutralizing factor/lysosomal enzyme detection moiety complex from step (a) with cells comprising a cation independent mannose-6-phosphate receptor (CI-MPR); (c) detecting the presence of LE-specific neutralizing factor from the body fluid sample by detecting the lysosomal enzyme labeled with the detection moiety inside the cell or on the surface of the cell, wherein a low amount of detectable LE-detection moiety is indicative of the presence of LE-specific neutralizing factors in the sample, (d) determining whether the LE-specific neutralizing factors interfere with efficacy of the enzyme replacement therapy, and (e) altering the therapy regimen when the LE-specific neutralizing factors interfere with efficacy of the enzyme replacement therapy, optionally wherein the subject is further administered an immunosuppressive drug and/or the dose of enzyme replacement therapy for the subject is reduced.

Also contemplated herein is a method for treating a subject having a lysosomal storage disease and receiving enzyme replacement therapy comprising (a) contacting a body fluid sample from the subject with a lysosomal enzyme conjugated to a detection moiety to detect LE-specific neutralizing factors in the body fluid sample, wherein the LE-specific neutralizing factor and lysosomal enzyme detection moiety form a complex; (b) contacting the LE-specific neutralizing factor/lysosomal enzyme complex from step (a) with cells comprising a cation independent mannose-6-phosphate receptor (CI-MPR), (c) detecting the presence of LE-specific neutralizing factor from the body fluid sample by detecting the lysosomal enzyme labeled with the detection moiety inside the cell or on the surface of the cell, wherein a low amount of detectable LE-detection moiety conjugate is indicative of the presence of LE-specific neutralizing factors in the sample, (d) determining whether the LE-specific neutralizing factors interfere with efficacy of the enzyme replacement therapy, and (e) altering the therapy regimen when the LE-specific neutralizing factors interfere with efficacy of the enzyme replacement therapy, optionally wherein the subject is further administered an immunosuppressive drug and/or the dose of enzyme replacement therapy for the subject is reduced.

An immunosuppressive drug as contemplated herein includes, but is not limited to, calcineurin inhibitors such as cyclosporin A, rapamycin, and FK506, and antiproliferative drugs, including but not limited to, azathioprine, 6-mercaptopurine, thioguanine, cytarabine, methotrexate, mycophenolic acid, or 6-(1,3-Dihydro-4-hydroxy-6-methoxy-7-methyl-3-oxy-5-isobenzofuranyl)-4-methyl-4-hexanoic acid, and the like, cyclophosphamide and chlorambucil. Methods of administering immunosuppressive therapy to subjects receiving enzyme replacement therapy are disclosed in, e.g., U.S. Pat. Nos. 7,485,314 and 9,044,473.

It is understood that each feature or embodiment, or combination, described herein is a non-limiting, illustrative example of any of the aspects of the disclosure and, as such, is meant to be combinable with any other feature or embodiment, or combination, described herein. For example, where features are described with language such as "one embodiment", "some embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the disclosure. Similarly, where a method describes using or identifying polypeptide binding agents, such as antibodies, characterized by certain features, polypeptide binding agents characterized by those features are also contemplated by the disclosure. Where examples of values falling within ranges are disclosed, any of these examples are contemplated as possible endpoints of a range, any and all numeric values between such endpoints are contemplated, and any and all combinations of upper and lower endpoints are envisioned.

BRIEF DESCRIPTION OF THE DRAWINGS

FIGS. 5A-5E show uptake of Alexa488-rhGALNS by Jurkat cells measured by flow cytometry. (FIG. 5A) Dose-response curve showing uptake (MFI) of Alexa488-rhGALNS (0-363.6 nM). (FIG. 5B) Hanes-Woolf plot between MFI and concentration of Alexa488-rhGALNS. (FIG. 5C) Uptake of Alexa488-rhGALNS (MFI) following no treatment or treatment of cells with trypan blue, cytochalasin B, or incubation at 4° C. Error bars (±standard deviation) for each condition are included but may be indistinguishable from the top of histogram bar. (FIG. 5D) Uptake of Alexa488-rhGALNS (MFI) and Alexa488-anti-CD3 following treatment of cells with 0.005%-0.4% trypan blue. Error bars represent the means±SDs. (FIG. 5E) Percent signal inhibition (% SI; Alexa488-rhGALNS uptake MFI relative to non-treated control) following treatment of cells with increasing concentrations of sCI-M6PR, M6P, or goat anti-GALNS antibody.

(FIG. 6A) Jurkat cells treated with varying concentrations of Alexa488-rhGALNS (0.156-2.5 µg/mL) premixed with the indicated concentrations of AbPC (anti-rhGALNS). (FIG. 6B) Data from (FIG. 6A) presented as the relative MFI fold change over the MFI from the maximum concentration of AbPC tested (100 µg/m1). (FIG. 6C) Alexa488-rhGALNS uptake at the indicated concentrations of AbPC in the presence of different serum dilutions (1:2.5-1:20).

FIGS. 7A-7C illustrate the assay sensitivity and example quality control data. Individual % SI means for 1:3 serial dilutions, starting at 20 µg/mL, from 6 independent validation runs to establish the assay sensitivity in NPS (FIG. 7A) or in pooled serum from individuals with Morquio A syndrome (FIG. 7B). The assay screening cut point (SCP) of 14.02% in (A) or 19.6% in (B) is shown to demonstrate where serial dilutions crossed the cut point. (FIG. 7C) Representative flow cytometry histograms and Alexa488-rhGALNS MFI for NQC (0 µg/mL), LQC (3 µg/mL), and HQC (20 µg/mL) samples.

(FIG. 8B) Drug-naïve serum samples from 5 male and 5 female individuals with Morquio A syndrome spiked with 3 µg/mL AbPC (LQC) or unspiked controls. The assay screening cut point of 14.02% in (FIG. 8A) or 19.6% in (FIG. 8B) is shown as a line to demonstrate where samples cross the cut point. Bars represent the means (±standard deviation) of samples tested in 2 independent experiments over 2 days.

(FIG. 9A) Concordance between NAb positivity detected with the in vitro CI-M6PR binding assay and the cell-based functional NAb assay in samples from individuals treated with placebo, elosulfase alfa 2.0 mg/kg QOW, or elosulfase alfa 2.0 mg/kg QW. (FIG. 9B) Mean TAb and NAb titer (from cell-based functional NAb assay) over 24 weeks in samples from individuals treated with placebo, elosulfase alfa 2.0 mg/kg QOW, or elosulfase alfa 2.0 mg/kg QW.

FIG. 10 is a table showing the concordance of NAb assay results by study week. Ligand receptor binding NAb and cell-based uptake NAb assay positive (+) and negative (−) values are shown with percentages in parentheses.

FIGS. 11A-11B show the efficacy and NAb titers for individuals receiving elosulfase alfa 2.0 mg/kg QOW or QW in the MOR-004 study. (FIG. 11A) Change in 6MWT distance from baseline to week 24 plotted against NAb titer in the QOW (left) and QW (right) dose cohorts. (FIG. 11B) Percentage change from baseline to week 24 in uKS levels plotted against NAb titer in the QOW (top) and QW (bottom) dose cohorts.

(FIG. 12A) Serum half-life ($t_{1/2}$; min) of elosulfase alfa at week 22 is plotted against week 24 NAb titer (log scale) in the 2.0 mg/kg QOW (top panel) and QW (bottom panel) dose groups. (FIG. 12B) Elosulfase alfa clearance (CL; mL/min/kg) from serum at week 22 is plotted against week 24 NAb titer (log scale) in the 2.0 mg/kg QOW (top) and QW (bottom) dose groups.

DETAILED DESCRIPTION OF THE INVENTION

Figure 1:
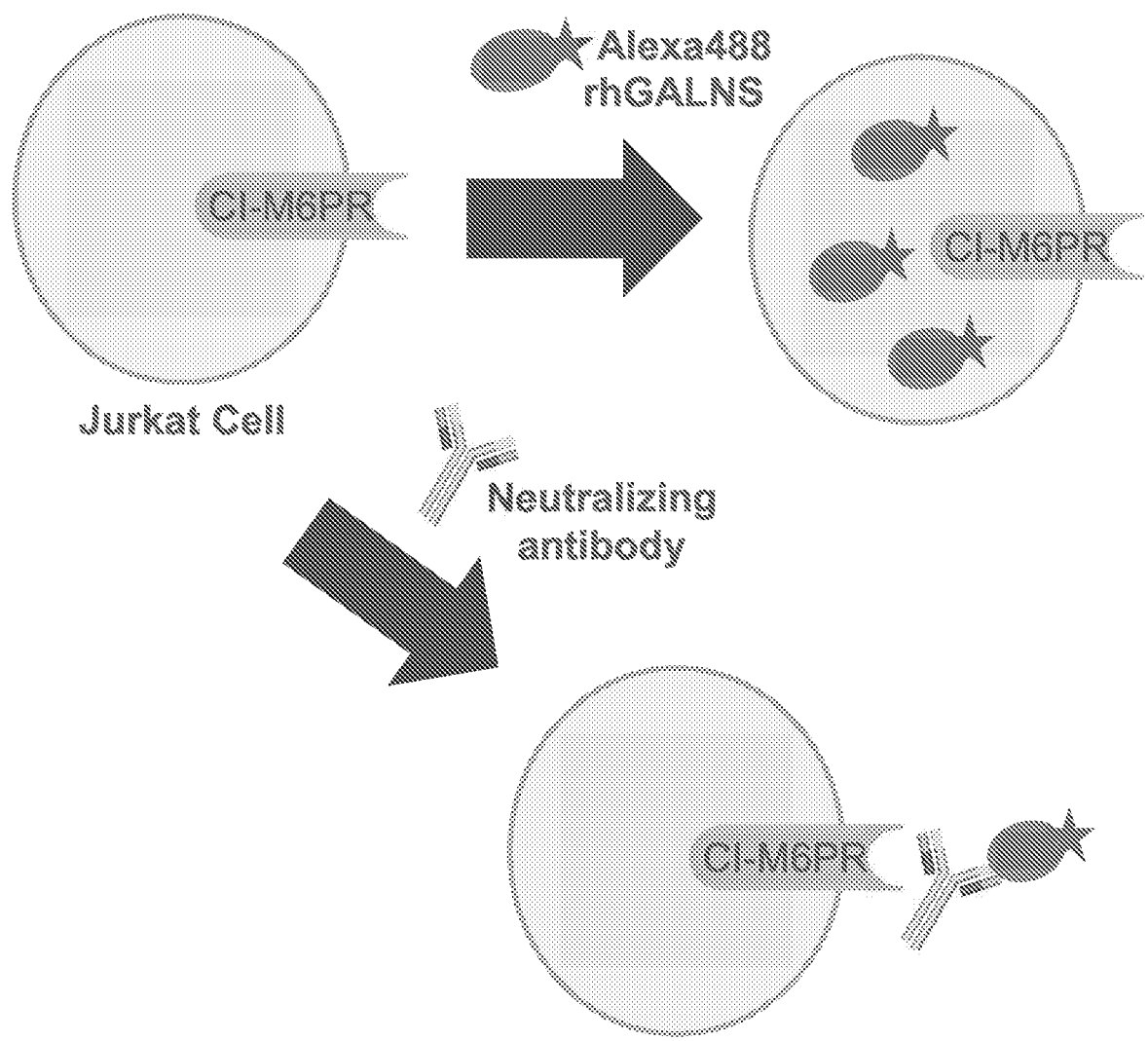
FIG. 1 shows a schematic diagram of the assay procedure.

The present invention is based on the development of sensitive, specific cell-based assays to detect neutralizing factors, such as antibodies, specific for lysosomal enzymes from patient body fluids and tissues that arise as a result of enzyme replacement therapy.

Unless otherwise defined, all technical and scientific terms used herein have the same meaning as commonly understood by one of ordinary skill in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that as used in this specification and the appended claims, the singular forms "a," "an," and "the" include plural reference unless the context clearly dictates otherwise.

As used herein, the following terms have the meanings ascribed to them unless specified otherwise.

The term "derivative" when used in connection with antibody substances and polypeptides of the invention refers to polypeptides chemically modified by techniques including, but not limited to, ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins. Derivatives retain the binding properties of underivatized molecules of the invention.

The terms "detectable moiety," "detection moiety" or a "label" as used herein refers to a composition detectable by means including, but not limited to, spectroscopic, photochemical, biochemical, immunochemical, chemical, or other physical means. For example, useful detectable moieties or labels include Ruthenium (Ru)-based catalyst, Europium, $^{32}P$, $^{35}S$, fluorescent dyes, electron-dense reagents, enzymes (e.g., as commonly used in an ELISA), biotin-Streptavidin, dioxigenin, haptens and proteins for which antisera or monoclonal antibodies are available, and nucleic acid molecules with a sequence complementary to a target. Fluorescent labels or fluorophores include, but are not limited to, Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, phycoerythrin (PE), fluorescein isothiocyanate (FITC), BODIPY FL, BODIPY 630/650, Cy2, Cy3, Cy3B, Cy3.5, Cy5, Cy5.5, Cy7, ECD, FITC, FluorX®, Cascade® Blue, Pacific Blue®, Pacific Green®, Pacific Orange®, eFluor® 450, eFluor® 605NC, eFluor® 625NC, eFluor® 650NC, eFluor® 660, eFluor® 710, Brilliant Violet™ (BV) fluorophores BV421, BV510, BV570, BV 605, BV650, BD Horizon™ V450, BD Horizon™ V500, Texas Red, rhodamine, cyanine, phycocyanin, allophycocyanin (APC), o-phthaldehyde, fluorescamine, Oregon Green® 488, PE-APC, PE-Cy5, PerCP, PE-TR, rhodamine green and rhodol green, and tandem dyes thereof.

The detectable moiety or label often generates a measurable signal, such as a radioactive, chromogenic, luminescence, or fluorescent signal, which can be used to quantitate the amount of bound detectable moiety or label in a sample.

The term "capture moiety" as used herein refers to a composition that is capable of being specifically bound by another composition that is attached or linked to a solid support. Many of the above detection moieties can also be used as capture moieties so long as a binding event is involved. For example, useful capture moieties include affinity labels for which specific and selective ligands are available (e.g., biotin with avidin, glutathione with GST), haptens and proteins for which antisera or monoclonal antibodies are available (e.g., c-Myc), nucleic acid molecules with a sequence complementary to a target, and peptides for which specific and selective ligands are available (e.g., histidine tag with Ni). Molecules that affect the binding characteristics to a chromatographic resin are also envisioned. The solid support can be, for example, a filter, a plate, a membrane, a chromatographic resin, or a bead.

The terms "identical" or percent "identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using a sequence comparison algorithm or by visual inspection.

The term "variant" as used herein refers to a polypeptide sequence that contains at least one amino acid substitution, deletion, or insertion in the coding region relative to the original polypeptide coding domains. Variants retain the biological activity of the naturally occurring polypeptide. For example, it is contemplated that a lysosomal enzyme used in the method of the invention may be the naturally occurring enzyme or may comprise one or more amino acid changes from the naturally occurring enzyme, but retains the biological activity of the enzyme. Likewise, a lysosomal enzyme receptor used in the method of the invention may be a variant or fragment of the naturally occurring receptor, but retains binding to its ligand.

The term "detectable lysosomal enzyme" as used herein generally refers to a lysosomal enzyme capable of being detected, e.g., the lysosomal enzyme reagent is directly labeled in addition to its inherent binding to a lysosomal enzyme-specific antibody.

The term "limit of detection" or "LOD" or "sensitivity" as used herein generally refers generally to the lowest analyte concentration in a body fluid (e.g., serum) sample that can be detected but not necessarily quantitated as an exact value. For example, LOD may be defined as the analyte concentration that consistently generates a signal greater than the measured mean response of the pooled naïve matrix plus a cutpoint factor.

The term "cutpoint factor" or "threshold" as used herein generally refers to a value that is mathematically normalized to the signal from the naïve pooled control matrix (e.g., serum) and is used to define the minimum signal required from a sample to be considered positive. The cutpoint factor may be determined based on a confidence interval from a set of samples from individuals that have not been previously exposed to the therapeutic lysosomal enzyme (Shankar et al., J Pharm Biomed Anal 48 (2008) 1267-1281). For example, the 95% confidence interval, calculated as 1.645 multiplied by the standard deviation across the individual samples, will lead to approximately a 5% false positive rate.

The term "interference" as used herein refers generally to the presence of substances in body fluid (e.g., serum) samples that prevent the target analyte from accurate detection and measurement. As used herein, interference refers generally to the effect of free drug or the effect of the matrix (e.g., serum) on the concentration-response relationship. For example, interference from matrix may be evaluated as the relative accuracy to samples without the potential interference to target a range of 75-125% relative accuracy.

The term "precision" as used herein generally refers to the variability in signal between the analysts and days. For example, precision may be evaluated as coefficient of variation, ranges of values, or using ANOVA statistics.

The term "reagent stability" as used herein generally refers to the robustness of preparation and storage stability of the reagents. For example, reagent stability may be established by the conditions that still permit values to be measured within 75-125% accuracy relative to freshly prepared reagents.

The term "sample stability" as used herein generally refers to the stability of the analyte in the biological fluid or tissue samples to handling conditions that the collected samples are anticipated to experience. Sample stability may be measured as the conditions that still permit values to be measured within 75-125% accuracy relative to freshly collected samples. For example, sample stability may be evaluated at −20° C. and −80° C. over time periods equal to a typical storage period, at room temperature (RT) or 4° C. over a time period equal to the typical sample preparation and analytical run times, at −20° C., 4° C. and RT over a time period equal to the typical shipping period, or through freeze-thaw cycles that may be experienced.

The term "robustness" as used herein generally refers to the capacity of the assay to remain unaffected by small variations in method parameters and indicates reliability of the assay during normal run conditions. For example, robustness can be evaluated as the percent change of reagent concentration, reagent volume, or incubation time that still generates signal within 75-125% accuracy relative to the nominal conditions.

The term "percent inhibition" refers to the ability of lysosomal enzyme specific antibodies to inhibit lysosomal enzyme uptake into a cell or inhibit lysosomal enzyme activity. The methods herein are able to detect the percent inhibition of an antibody present in a patient sample. In various embodiments, the percent inhibition is detectable at 10%, 15%, 20%, 25%, 30%, 35%, 40%, 45%, 50%, 55%, 60%, 65% 70%, 75%, 80%, 85%, 90%, 95%, 100% or any ranges between these endpoints, and inclusive of these endpoints.

The term "specificity" as used herein generally refers to the ability of the assay to detect factors or physiochemically-related proteins to the ERT that affect cellular uptake. For example, specificity may refer to a proportional detection response with the specific analyte, while response from an antibody sample that is not specific for the lysosomal enzyme should be below the LOD. The proportional response may be evaluated against a correlation coefficient R value greater than or equal to 0.98.

The term "neutralizing factor" refers to factors that prevent cellular uptake of lysosomal enzymes, and may arise as a result of enzyme replacement therapy in a subject. Exemplary neutralizing factors include neutralizing antibodies, free mannose-6-phosphate, IGF-II, IGF-II peptides, IGF-II peptide analogs or soluble CI-MPR.

An antibody that "specifically binds" is "target specific", is "specific for" target or is "immunoreactive" with the target antigen refers to an antibody or antibody substance that binds the target antigen with greater affinity than with similar antigens. In one aspect of the disclosure, the target-binding polypeptides, or fragments, variants, or derivatives thereof, will bind with a greater affinity to human target as compared to its binding affinity to target of other, i.e., non-human, species, but binding polypeptides that recognize and bind orthologs of the target are within the scope provided.

For example, an antibody or fragment thereof "specific for" its cognate antigen indicates that the variable regions of the antibodies recognize and bind the polypeptide of interest with a detectable preference (i.e., able to distinguish the polypeptide of interest from other known polypeptides of the same family, by virtue of measurable differences in binding affinity, despite the possible existence of localized sequence identity, homology, or similarity between family members). It will be understood that specific antibodies may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody for use in the methods of the present disclosure are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6.

The term "matrix" or "matrices" as used herein generally refers to the biological background in which the antibodies are measured. Examples of matrices include, for example, body fluid and tissue.

The term "body fluid" as used herein refers to a fluid that is obtained from a subject, e.g., human. For example, a body fluid may be blood, cerebrospinal fluid (CSF) or urine. The blood may be fractionated to remove cells (i.e., plasma) or fractionated to remove cells and clotting factors (i.e., serum).

The term "tissue" as used herein refers to tissues that are obtained from a subject, e.g., human. For example, a tissue may be from a biopsy sample, surgically removed tissue, or postmortem collection. Furthermore, the tissue may be homogenized and extracted to isolate the antibodies from the tissue.

The term "naïve" as used herein refers to individuals, e.g., humans, which have not been previously exposed to the therapeutic, but may have been exposed to endogenous levels of the factor.

A "lysosomal storage disease" refers to any disease resulting from the deficiency of one or more lysosomal enzymes necessary for metabolizing natural macromolecules. These diseases typically result in the accumulation of un-degraded molecules in the lysosomes, resulting in increased numbers of storage granules (also termed storage vesicles). These diseases are described in more detail below.

"Enzyme replacement therapy" refers to a method of treatment in which a recombinant form of an enzyme that is missing, deficient or defective in a subject having a lysosomal storage disorder is administered in order to compensate for the missing enzyme.

A "subject" is meant to include any animal that is to be treated using the methods of the invention. Preferably, the subject is a mammalian subject, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are included within the term "subject."

By "therapeutically effective," the present specification intends to denote any therapeutic benefit that arises as a result of the treatment methods described herein. For example, such an effect can be the beneficial effects that manifest in an appropriate target tissue, of the enzyme which is deficient or missing in the lysosomal disorder of interest, where such beneficial physiological effect is compared to that physiological parameter being measured in the absence of the enzyme replacement therapy. Such a therapeutic effect may be any reduction or elimination of one or more clinical or subclinical manifestations of the disease of interest. For example, a reduction in the number of storage vesicles (also termed storage granules), or elimination thereof, will provide a therapeutic benefit to the treated subject. Methods for assessing therapeutic benefit are known in the art, e.g., see U.S. Pat. No. 9,089,566.

Variants

In certain embodiments, lysosomal enzyme (LE) or LE receptor analogs and variants may be prepared and are useful in a variety of applications in which lysosomal enzymes and their receptors may be used. LE or LE fragments include the full-length enzyme, or any variant, fragment or modification thereof that retains at least some of the biological activity (i.e., enzymatic activity) of the full-length enzyme. LE receptor or LE-binding fragments include full-length receptor, an extracellular portion of the receptor, or any variant, fragment or modification thereof that retains at least some of the biological activity (i.e., LE-binding activity) of the full-length LE receptor.

Full-length LE can be isolated from natural sources or prepared using recombinant techniques. LE fragments can be prepared using recombinant techniques. LE receptors can be isolated from natural sources (e.g., purified from fetal bovine serum) or prepared using recombinant techniques. For example, a general strategy to generate recombinant full-length LE receptors or extracellular portions of LE receptors, or variants or variants, fragments or modifications thereof that retains LE-binding activity is to amplify the coding region of interest from the LE receptor cDNA by PCR, clone the cDNA into a mammalian expression vector, transfect the mammalian expression vector into mammalian cells, e.g., Chinese hamster ovary (CHO) or G.7.1 cells, and purify the LE receptor using procedures to isolate LE receptors shed from cells present in fetal bovine serum. LE receptors or variants thereof can be from human or other mammalian sources.

Amino acid sequence variants of LE or LE receptors can be, for example, substitutional, insertional or deletion variants. Deletion variants lack one or more residues of the native LE or LE receptor, which are not essential for function and/or immunogenic activity. Insertional mutants typically involve the addition of material at a non-terminal point in the polypeptide. This may include the insertion of an immunoreactive epitope or simply a single residue. Terminal additions are additions of amino acid sequences at either the N- or C-terminus of the LE or LE receptor. Terminal additions can be used to improve the LE or LE receptor's biophysical characteristics or simplify the purification. Peptide additions include, for example and not for limitation, HIS (e.g., 6 or 12), TAT, FLAG™, HA, c-Myc, VSV-G, V5, S-peptide, and HSV. Protein additions include, for example and not for limitation, GFP, MBP, and GST.

Substitutional variants typically exchange one amino acid of the naturally occurring LE or LE receptor for another at one or more sites, and may be designed to modulate one or more properties of the LE or LE receptor, such as stability against proteolytic cleavage, without the loss of other functions or properties. Substitutions of this kind preferably are conservative, i.e., one amino acid is replaced with one of similar shape and charge.

Variants may be substantially homologous or substantially identical to the naturally occurring LE or LE receptor. In the context of two nucleic acids or polypeptides, substantially homologous generally refers to two or more sequences or subsequences that have at least 40%, 60%, 80%, 90%, 95%, 96%, 97%, 98% or 99% nucleotide or amino acid residue identity, when compared and aligned for maximum correspondence, as measured using sequence comparison algorithms well known in the art or by visual inspection.

Cation Independent-Mannose 6 Phosphate Receptor (CI-MPR) is a lysosomal enzyme receptor that is naturally expressed on a variety of cells types including, T cells, muscle cells and macrophages. Cells naturally expressing or engineered to express the CI-MPR are contemplated for use in the present methods. Exemplary cells for use in the method include, but are not limited to, HeLa, Jurkat, MCF-7, NIH3T3, HepG2, peripheral blood mononuclear cells (PBMCs) and macrophages. Cells modified to recombinantly express the CI-MPR or a lysosomal enzyme binding fragment thereof on the cell surface are also contemplated for use in the method. Examples of useful mammalian host cell lines for recombinant protein expression include, but are not limited to, Chinese hamster ovary (CHO) cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, (Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (HB 8065); mouse mammary tumor (MMT 060562, ATCC CCL51); TRI cells (Mather et al., Annals N.Y Acad. Sci. 383: 44-68 (1982)); MRC 5 cells and FS4 cells.

Methods of recombinant protein expression are well-known in the art. Nucleotide sequences for human CI-MPR (Genbank Accession No. J03528) and CI-MPR from other species are known in the art and are accessible via publicly available genomic databases, such as that maintained by the National Centers for Biotechnology Information and the U.S. National Library of Medicine. In order to recombinantly express a CI-MPR in a cell, one of skill would insert a CI-MPR nucleotide sequence into a recombinant expression vector for expression in an appropriate host cell.

Host cells are transformed or transfected with expression or cloning vectors for a CI-MPR or fragment thereof and cultured in conventional nutrient media modified as appropriate for inducing promoters, selecting transformants, or amplifying the genes encoding the desired sequences in order to get expression on the cell surface.

Labels (Detectable and Capture Moieties)

In some embodiments, an assay reagent is labeled to facilitate its detection. A label or a detectable moiety is a composition detectable by spectroscopic, photochemical, biochemical, immunochemical, chemical, or other physical means. For example, antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), or luminescent or bio-luminescent labels (such as Europium, Vanadium, etc.), paramagnetic atoms, electrochemiluminescent labels (such as Ru-based labels in conjunction with substrates, etc.), and the like.

In some embodiments, an assay reagent is labeled to facilitate its capture or detection. A capture moiety is a composition that is capable of being specifically bound by another composition that is attached or linked to a solid support. An assay reagent, e.g., lysosomal enzyme, can be labeled through the use of affinity labels (such as biotin, avidin, etc.) for which specific and selective ligands are available, haptens and proteins for which antisera or monoclonal antibodies are available, and nucleic acid molecules with a sequence complementary to a target. Procedures for accomplishing such labeling are described in Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The solid support can be a filter, plate, membrane or bead, and the like.

Examples of labels suitable for use in the present invention include, but are not limited to, radioactive labels (e.g., $^{32}$P), fluorophores (e.g., fluorescein), electron-dense reagents, enzymes (e.g., as commonly used in an ELISA), biotin, digoxigenin, or haptens as well as proteins which can be made detectable, e.g., by incorporating a radiolabel into the hapten or peptide, or used to detect antibodies specifically reactive with the hapten or peptide. Also contemplated are a nanotag, a molecular mass bead, a magnetic agent, a nano- or micro-bead containing a fluorescent dye, a quantum dot, a quantum bead, a fluorescent protein, dendrimers with a fluorescent label, a micro-transponder, an electron donor molecule or molecular structure, or a light reflecting particle.

For example, labels contemplated for use with present invention include, but are not limited to, fluorescent dyes (e.g., AlexaFluor dyes, fluorescein isothiocyanate, Texas red, rhodamine, and the like as described above), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), biotin, and colorimetric labels such as colloidal gold, colored glass or plastic beads (e.g., polystyrene, polypropylene, latex, etc.), and luminescent or chemiluminescent labels (e.g., Europium (Eu), MSD Sulfo-Tag).

Fluorescent labels or fluorophores include, but are not limited to, Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, phycoerythrin (PE), fluorescein isothiocyanate (FITC), BODIPY FL, BODIPY 630/650, Cy2, Cy3, Cy3B, Cy3.5, Cy5, Cy5.5, Cy7, ECD, FITC, FluorX®, Cascade® Blue, Pacific Blue®, Pacific Green®, Pacific Orange®, eFluor® 450, eFluor® 605NC, eFluor® 625NC, eFluor® 650NC, eFluor® 660, eFluor® 710, Brilliant Violet™ (BV) fluorophores BV421, BV510, BV570, BV 605, BV650, BD Horizon™ V450, BD Horizon™ V500, Texas Red, rhodamine, cyanine, phycocyanin, allophycocyanin (APC), o-phthaldehyde, fluorescamine, Oregon Green® 488, PE-APC, PE-Cy5, PerCP, PE-TR, rhodamine green and rhodol green, and tandem dyes thereof.

The label may be coupled directly or indirectly to the desired component of the assay. Preferably, the label in one embodiment is covalently bound to the biopolymer using an isocyanate or N-hydroxysuccinimide ester reagent for conjugation of an active agent according to the invention. In one aspect of the invention, the bifunctional isocyanate reagents of the invention can be used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecule (e.g., Streptavidin) molecule, which is either inherently detectable or covalently bound to a signal system, such as a detectable enzyme, a fluorescent compound, or a chemiluminescent compound, or to a solid support, such as a filter, a plate, a membrane or a bead, and the like.

The compounds useful in the method of the invention can also be conjugated directly to signal-generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include those described above. Further examples of suitable fluorophores include, but are not limited to, eosin, TRITC-amine, quinine, fluorescein W, acridine yellow, lissamine rhodamine, dansyl, umbelliferone, B sulfonyl chloride erythroscein, ruthenium (tris, bipyridinium), europium, nicotinamide adenine dinucleotide, flavin adenine dinucleotide, etc. Chemiluminescent compounds suitable for use as labels include, but are not limited to, Europium (Eu), Samarium (Sm), luciferin and 2,3-dihydrophthalazinediones, e.g., luminol. Electrochemiluminescent compounds suitable for use as labels include, but are not limited to, MSD TAG, MSD Sulfo-TAG, BV-TAG, and BV-TAG Plus. For a review of various labeling or signal producing systems that can be used in the methods of the present invention, see U.S. Pat. No. 4,391,904.

Detection Methods and Kits

Where the label is a fluorescent label, exciting the fluorochrome with the appropriate wavelength of light and detecting the resulting fluorescence may detect it. The fluorescence may be detected visually, by the use of electronic detectors such as flow cytometric devices, charge coupled devices (CCDs) or photomultipliers and the like. Similarly, enzymatic labels may be detected by providing the appropriate substrates for the enzyme and detecting the resulting reaction product. Colorimetric labels may be detected simply by observing the color associated with the label. Other labeling and detection systems suitable for use in the methods of the present invention will be readily apparent to those of skill in the art. Such labeled modulators and ligands can be used in the diagnosis of a disease or health condition.

Chemiluminescent labels may be detected by observing the light emitted upon reaction of the label with substrate. Electrochemiluminescent labels may be detected by observing the light emitted upon reaction of the label with substrate in an electrical field.

Antigen-antibody complexes may also be detected using nanoparticle-derived techniques. See, for example, Ao et al., *Anal Chem.* 78:1104-6 (2006), which describes gold nanoparticle quenching, Tang et al., *Biosens Bioelectron.* 2005 Nov. 30, which describes SiO(2)/Au nanoparticle surfaces in antibody detection, and Lieu et al., *J Immunol Methods.* 307:34-40 (2005), which describes silicon dioxide nanoparticles containing dibromofluorescein for use in solid substrate-room temperature phosphorescence immunoassay (SS-RTP-IA).

Kits are also contemplated within the scope of the invention. In one embodiment, the kit comprises a lysosomal enzyme, optionally linked to a detectable label or a capture moiety, optionally a lysosomal enzyme conjugated to a bead, and/or an antibody standard that specifically binds to the lysosomal enzyme, and/or a lysosomal enzyme standard containing a known quantity of a lysosomal enzyme. In various embodiment, the kit comprises cells that express the CI-MPR. Other components of the kits may optionally include reagents and/or instructions for carrying out immunoassays, as described supra.

Spectral absorption labels may also be used. A possible methodology for detection would be to mix into the bead polymer different materials that absorb and pass different spectra of light. Each different type of bead could be detected by passing a multi-spectral light though the bead and detecting which spectra are absorbed.

Lysosomal Enzymes and Uses of the Present Methods

In a particular embodiment, the invention provides methods for detecting antibodies to a therapeutic protein having a biological activity which is reduced, deficient, or absent in the target lysosome and which is administered to the subject Enzyme therapeutics include, but are not limited to, aspartylglucosaminidase, acid lipase, cysteine transporter, Lamp-2, alpha-galactosidase A, acid ceramidase, alpha-L-fucosidase, beta-hexosaminidase A, GM2-activator deficiency, alpha-D-mannosidase, beta-D-mannosidase, arylsulfatase A, saposin B, neuraminidase, alpha-N-acetylglucosaminidase phosphotransferase, phosphotransferase γ-subunit, alpha-L-iduronidase, iduronate-2-sulfatase, heparan-N-sulfatase, alpha-N-acetylglucosaminidase, acetylCoA:N-acetyltransferase, N-acetylglucosamine 6-sulfatase, alpha-glucosidase, alpha-galactosidase, N-acetylgalactosamine 4-sulfatase, N-acetylgalactosamine 6-sulfatase, hyaluronoglucosaminidase, palmitoyl protein thioesterase, tripeptidyl peptidase I, acid sphingomyelinase, cholesterol trafficking, cathepsin K, beta-galactosidase B, α-glucosidase, and sialic acid transporter. In various embodiments, the enzyme is N-acetylgalactosamine 6-sulfatase, alpha-glucosidase, alpha-N-acetylglucosaminidase or tripeptidyl peptidase I.

Lysosomal enzymes described above are useful therapeutics in the lysosomal storage diseases having the corresponding deficiency in the enzyme. Exemplary lysosomal storage diseases include, but are not limited to, Aspartylglucosaminuria, Cholesterol ester storage disease/Wolman disease, Cystinosis, Danon disease, Fabry disease, Farber Lipogranulomatosis/Farber disease, Fucosidosis, Galactosialidosis types I/II, Gaucher disease types I/II/III Gaucher disease, Globoid cell leukodystrophy/Krabbe disease, Glycogen storage disease II/Pompe disease, GM1-Gangliosidosis types I/II/III, GM2-Gangliosidosis type I/Tay-Sachs disease, GM2-Gangliosidosis type II Sandhoff disease, GM2-Gangliosidosis, alpha-Mannosidosis types I/II, alpha-Mannosidosis, Metachromatic leukodystrophy, Mucolipidosis type I/Sialidosis types I/II Mucolipidosis types II/III I-cell disease, Mucolipidosis type IIIC pseudo-Hurler polydystrophy, Mucopolysaccharidosis type I (MPS I), Mucopolysaccharidosis type II Hunter syndrome (MPS II), Mucopolysaccharidosis type IIIA Sanfilippo syndrome (MPS IIIA), Mucopolysaccharidosis type IIIB Sanfilippo syndrome (MPS IIIB), Mucopolysaccharidosis type IIIC Sanfilippo syndrome (MPS IIIC), Mucopolysaccharidosis (MPS) type IIID Sanfilippo syndrome (MPS IIID), Mucopolysaccharidosis (MPS) type IVA Morquio syndrome (MPS IVA), Mucopolysaccharidosis type IVB Morquio syndrome (MPS IVB), Mucopolysaccharidosis type VI (MPS VI), Mucopolysaccharidosis type VII Sly syndrome (MPS VII), Mucopolysaccharidosis type IX (MPS IX), Multiple sulfatase deficiency, Pompe Disease, Neuronal Ceroid Lipofuscinosis, CLN1 Batten disease, Neuronal Ceroid Lipofuscinosis, CLN2 Batten disease, Niemann-Pick disease types A/B, Niemann-Pick disease type C1, Niemann-Pick disease type C2, Pycnodysostosis, Schindler disease types I/II Schindler disease, and Sialic acid storage disease, Metachromatic Leukodystrophy, Gaucher, Krabbe, and Tay-Sachs disease wherein a lysosomal protein deficiency contributes to the disease state. In various embodiments, the lysosomal storage disease is Morquio syndrome (MPS IVA), Mucopolysaccharidosis type IVB Morquio syndrome (MPS IVB), Pompe Disease, Mucopolysaccharidosis type IIIB Sanfilippo syndrome (MPS IIIB) or CLN2/Batten Disease.

Morquio Syndrome

Mucopolysaccharidosis type IVA (Morquio Syndrome, MPS IVa) is an inherited, autosomal recessive disease belonging to the group of mucopolysaccharide storage diseases. Morquio Syndrome is caused by a deficiency of a lysosomal enzyme required for the degradation of two glycosaminoglycans (GAGs), keratan sulfate (KS) and chondroitin-6-sulfate (C6S). Specifically, MPS IVA is characterized by the absence of the enzyme N-acetylgalactosamine-6-sulfatase (rhGALNS), and the excretion of KS in the urine. The lack of rhGALNS results in accumulation of abnormally large amounts of mucopolysaccharides in hyaline cartilage, a main component of skeletal tissues. All patients have a systemic skeletal dysplasia. Other symptoms vary in severity from patient to patient, and may include hearing loss, cataracts, spinal instability, heart valvular disease and respiratory issues, among others.

Recombinant human N-acetylgalactosamine-6-sulfatase (rhGALNS) has been developed as an enzyme replacement therapy (elosulfase alfa) for the treatment of MPS IVA. rhGALNS is internalized into the lysosome through the Cation-Independent Mannose-6-Phosphate Receptor (CI-MPR). In this subcellular compartment, the low pH (pHs 4-4.5) and proteolysis would decrease or eliminate the interaction of antibody and rhGALNS. Therefore, receptor cell surface interaction and internalization prior to lysosomal fusion is the most likely site of action for neutralizing factors.

Pompe Disease

Insufficient activity of the acid alpha glucosidase (GAA) enzyme in the lysosome results in Pompe disease, a disease also known as acid maltase deficiency (AMD), glycogen storage disease type II (GSDII), glycogenosis type II, or GAA deficiency. GAA hydrolyzes the alpha 1-4 linkage in maltose and other linear oligosaccharides, including the outer branches of glycogen, thereby breaking down excess glycogen in the lysosome (Hirschhorn et al. (2001) in The Metabolic and Molecular Basis of Inherited Disease, Scriver, et al., eds. (2001), McGraw-Hill: New York, p. 3389-3420) Like other mammalian lysosomal enzymes, GAA is synthesized in the cytosol and traverses the ER where it is glycosylated with N-linked, high mannose type carbohydrate. In the golgi, the high mannose carbohydrate is modified on lysosomal proteins by the addition of mannose-6-phosphate (M6P) which targets these proteins to the lysosome. The M6P-modified proteins are delivered to the lysosome via interaction with either of two M6P receptors.

The diminished GAA enzymatic activity occurs due to a variety of missense and nonsense mutations in the gene encoding GAA. Consequently, glycogen accumulates in the lysosomes of all cells in patients with Pompe disease. In particular, glycogen accumulation is most pronounced in lysosomes of cardiac and skeletal muscle, liver, and other tissues. Accumulated glycogen ultimately impairs muscle function. In the most severe form of Pompe disease, death occurs before two years of age due to cardio-respiratory failure. U.S. Pat. No. 7,785,856 discloses methods for treating Pompe Disease with recombinant GAA comprising an IGF-II GILT tag. Neutralizing antibodies that interfere with enzyme therapy have been detected in patients receiving therapy for infantile Pompe Disease (Harmatz et al., Clin Ther. 2015 September; 37(9):2130-4; Banugaria et al., Genet Med. 2011 August; 13(8):729-36).

Mucopolysaccharidosis III B (MPS IIIB)/Sanfilippo B Syndrome

Mucopolysaccharidosis III B (MPS IIIB) disease, also known as Sanfilippo Type B Syndrome. MPS IIIB, Sanfilippo B Syndrome, is a rare autosomal recessive genetic disorder that is characterized by a deficiency of the enzyme alpha-N-acetyl-glucosaminidase (Naglu). In the absence of this enzyme, glycosaminoglycans (GAG), for example the GAG heparan sulfate, and partially degraded GAG molecules cannot be cleared from the body and accumulate in lysosomes of various tissues, resulting in progressive widespread somatic dysfunction (Kakkis et al., N Engl J. Med. 344(3):182-8, 2001). It has been shown that GAGs accumulate in lysosomes of neurons and glial cells, with lesser accumulation outside the brain.

Four distinct forms of MPS III, designated MPS IIIA, B, C, and D, have been identified. Each represents a deficiency in one of four enzymes involved in the degradation of the GAG heparan sulfate. All forms include varying degrees of the same clinical symptoms, including coarse facial features, hepatosplenomegaly, corneal clouding and skeletal deformities. Most notably, however, is the severe and progressive loss of cognitive ability, which is tied not only to the accumulation of heparan sulfate in neurons, but also the subsequent elevation of the gangliosides GM2, GM3 and GD2 caused by primary GAG accumulation (Walkley et al., Ann N Y Acad. Sci. 845:188-99, 1998).

MPS III diseases all have similar symptoms that typically manifest in young children. Affected infants are apparently normal, although some mild facial dysmorphism may be noticeable. The stiff joints, hirsuteness and coarse hair typical of other mucopolysaccharidoses are usually not present until late in the disease. After an initial symptom-free interval, patients usually present with a slowing of development and/or behavioral problems, followed by progressive intellectual decline resulting in severe dementia and progressive motor disease. Acquisition of speech is often slow and incomplete. The disease progresses to increasing behavioral disturbance including temper tantrums, hyperactivity, destructiveness, aggressive behavior, pica and sleep disturbance. As affected children have normal muscle strength and mobility, the behavioral disturbances are very difficult to manage. In the final phase of the illness, children become increasingly immobile and unresponsive, often require wheelchairs, and develop swallowing difficulties and seizures. The life-span of an affected child does not usually extend beyond late teens to early twenties. Methods for treating MPS III B are described in US Pat Publ. No. 20140161788.

Neuronal Ceroid Lipofuscinosis (CLN2)/Batten Disease

Neuronal Ceroid Lipofuscinosis (CLN2) disease is a rare genetic disease characterized by a deficiency of the lysosomal enzyme tripeptidyl peptidase-1 (TPP1) caused by mutations in the TPP1 gene. CLN2 disease is inherited as an autosomal recessive disorder. In the absence of TPP1, lysosomal storage materials normally metabolized by the enzyme accumulate in many organs, and accumulation in the central nervous system leads to the neurodegenerative symptoms typical of CLN2 disease. The untreated disease progression of CLN2 disease has been well characterized, and the natural history of the disease is remarkably consistent and predictable, as demonstrated by natural history data from independent patient populations in North America and Europe.

The mature native TPP1 protein is a lysosomal serine protease, and is the only known mammalian member of the sedolisin (serine-carboxyl peptidase) family characterized by a highly conserved Ser-Glu-Asp (SED) catalytic triad. The primary activity of the enzyme is as a tripeptidyl exopeptidase with a broad substrate specificity. Activity of the enzyme on its substrate leads to a sequential release of tripeptides from the N-terminus of the protein substrate (Oyama et al., J Biochem. 2005; 138(2):127-34). Recombinant human tripeptidyl peptidase-1 (rhTPP1) is being developed as a possible treatment for CLN2 disease.

Also contemplated is a method for treating a patient with a lysosomal storage disease and undergoing enzyme replacement therapy comprising measuring levels of LE neutralizing factors in a sample from the patient using methods described herein, and if neutralizing factors are detected that interfere with efficacy of the ERT, then administering to the patient an immunosuppressive therapy, and/or reducing the amount of enzyme administered during enzyme replacement therapy. The lysosomal storage diseases and the enzymes administered during enzyme replacement therapy include those describe herein.

For example, provided herein is a method for treating a subject having a lysosomal storage disease and receiving enzyme replacement therapy comprising (a) contacting a body fluid sample from the subject with a lysosomal enzyme conjugated to a detection moiety to detect LE-specific neutralizing factors in the body fluid sample, wherein the LE-specific neutralizing factor and lysosomal enzyme detection moiety form a complex; (b) contacting the LE-specific factor/lysosomal enzyme detection moiety complex from step (a) with cells comprising a cation independent mannose-6-phosphate receptor (CI-MPR); (c) detecting the presence of LE-specific neutralizing factor in the body fluid sample by detecting the presence of the lysosomal enzyme labeled with the detection moiety inside the cell or on the surface of the cell, (d) determining whether the LE-specific neutralizing factors interfere with efficacy of the enzyme replacement therapy, and (e) altering the therapy regimen when the LE-specific neutralizing factors interfere with efficacy of the enzyme replacement therapy, optionally wherein the subject is further administered an immunosuppressive drug and/or the dose of enzyme replacement therapy for the subject is reduced.

Also provided herein is a method for treating a subject having a lysosomal storage disease and receiving enzyme replacement therapy comprising (a) contacting a body fluid sample from the subject with a lysosomal enzyme conjugated to a detection moiety to detect LE-specific neutralizing factors in the body fluid sample, wherein the LE-specific neutralizing factor and lysosomal enzyme detection moiety form a complex; (b) contacting the LE-specific neutralizing factor/lysosomal enzyme detection moiety complex from step (a) with cells comprising a cation independent mannose-6-phosphate receptor (CI-MPR); (c) detecting the presence of LE-specific neutralizing factor from the body fluid sample by detecting the lysosomal enzyme labeled with the detection moiety inside the cell or on the surface of the cell, wherein a low amount of detectable LE-detection moiety is indicative of the presence of LE-specific neutralizing factors in the sample, (d) determining whether the LE-specific neutralizing factors interfere with efficacy of the enzyme replacement therapy, and (e) altering the therapy regimen when the LE-specific neutralizing factors interfere with efficacy of the enzyme replacement therapy, optionally wherein the subject is further administered an immunosuppressive drug and/or the dose of enzyme replacement therapy for the subject is reduced.

Also contemplated herein is a method for treating a subject having a lysosomal storage disease and receiving enzyme replacement therapy comprising (a) contacting a body fluid sample from the subject with a lysosomal enzyme conjugated to a detection moiety to detect LE-specific neutralizing factors in the body fluid sample, wherein the LE-specific neutralizing factor and lysosomal enzyme detection moiety form a complex; (b) contacting the LE-specific neutralizing factor/lysosomal enzyme complex from step (a) with cells comprising a cation independent mannose-6-phosphate receptor (CI-MPR), (c) detecting the presence of LE-specific neutralizing factor from the body fluid sample by detecting the lysosomal enzyme labeled with the detection moiety inside the cell or on the surface of the cell, wherein a low amount of detectable LE-detection moiety conjugate is indicative of the presence of LE-specific neutralizing factors in the sample, (d) determining whether the LE-specific neutralizing factors interfere with efficacy of the enzyme replacement therapy, and (e) altering the therapy regimen when the LE-specific neutralizing factors interfere with efficacy of the enzyme replacement therapy, optionally wherein the subject is further administered an immunosuppressive drug and/or the dose of enzyme replacement therapy for the subject is reduced.

It is contemplated that the neutralizing factor is a neutralizing antibody.

In various embodiments, the dose of the enzyme administered is reduced by 1.5-, 2-, 3-, 4-, 5-, 6-, 7-, 8-, 9- or 10-fold or as determined appropriate by a treating physician.

An immunosuppressive drug as contemplated herein includes, but is not limited to calcineurin inhibitors such as cyclosporin A, rapamycin, FK506 (tacrolimus) and simrolimus, and antiproliferative drugs, including but not limited to, azathioprine, 6-mercaptopurine, thioguanine, cytarabine, methotrexate, mycophenolic acid, or 6-(1,3-Dihydro-4-hydroxy-6-methoxy-7-methyl-3-oxy-5-isobenzofuranyl)-4-methyl-4-hexanoic acid, and the like, cyclophosphamide and chlorambucil. Methods of administering immunosuppressive therapy to subjects receiving enzyme replacement therapy are disclosed in e.g., U.S. Pat. Nos. 7,485,314 and 9,044,473, herein incorporated by reference.

In various embodiments, the dose of cyclosporine A for human subjects may be approximately 10 mg/kg/day to about 15 mg/kg/day, to reach blood trough levels of between 100 and 500 ng/ml. The levels required may be comparable to those used in de novo renal or other transplants (about 8+/−3 mg/kg/day) at which a blood trough level of about 350+/−150 ng/ml was achieved, Physicians Desk Reference, ed. 56 published by Medical Economics Co., Montvale, N.J., p 2381). A conventional dose for oral tacrolimus is 0.2 mg/kg/day. A conventional dose for sirolimus is 2 mg/kg/day. A T cell immunosuppressive agent is administered for at least about two weeks, about 3 weeks, about 4 weeks, and may be for about 6 weeks or more.

If an antiproliferative agent is used, it may be administered at a conventional dose, optionally while a T cell immunosuppressive agent is administered, usually for at least about two weeks, more usually at least about 3 weeks, about 4 weeks, and may be for about 6 weeks or more. For example, the standard dose of azathioprine is from about 1 to 5 mg/kg/day, where the upper end, from about 3 to 5 mg/kg/day is used initially, and the lower range, from about 1 to 3 mg/kg/day may be given after establishment of the regimen. The anti-proliferative agent and/or T cell immunosuppressive agent may also be given every other week.

For example, the initial dose of the T cell immunosuppressive agent may be at a dose equivalent to at least about 125% of the standard dose for immunosuppression, at least about 150% of the standard dose, or 200% of the standard dose, or more. In other embodiments, the dose may be the conventional dose, administered more frequently, e.g. twice daily instead of daily, etc. A conventional dose for oral tacrolimus is 0.2 mg/kg/day. A conventional dose for sirolimus is 2 mg/kg/day. It will be appreciated by one of skill in the art that the standard dose will vary depending on the specific drug, on the method of administration, i.e. oral, intravenous, etc., and on the host.

It is further contemplated that the levels of LE-specific neutralizing factors are measured after administration of immunosuppressive therapy and/or reduction in ERT dose, and the immunosuppressive therapy is discontinued if LE-specific neutralizing factors are no longer detected, and/or the dose is increased back to the therapeutic dose prior to detection of LE-specific neutralizing factors.

Antibodies

In various embodiments, antibody standards or sample antibodies may be purified from a solution using techniques standard in the art, including but not limited to protein A-Sepharose, hydroxylapatite chromatography, gel electrophoresis, dialysis, or affinity chromatography. The antibody composition prepared from microbial or mammalian cells or serum can be purified using, for example, hydroxylapatite chromatography cation or anion exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62: 1-13 (1983)). Protein G is recommended for all mouse isotypes and for human γ3 (Guss et al., *EMBO J.* 5:1567-75 (1986)). The matrix to which the affinity ligand is attached is most often agarose or acrylamide, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

The assay can be used to detect LE-specific antibodies in a body fluid or tissue sample from a subject. In one embodiment, the body fluid is serum. In another embodiment, the body fluid is cerebrospinal fluid (CSF).

As used herein, an antibody or other factor that neutralizes cellular uptake of a lysosomal enzyme is one in which the neutralizing factor or neutralizing antibody specifically binds to the CI-MPR or blocks the interaction of the LE with the CI-MPR.

Assay to Detect Lysosomal Enzyme (LE)-Neutralizing Antibodies or Neutralizing Factors Because the low pH (pH 4-4.5) and proteolysis in the lysosomal compartment could decrease or eliminate the interaction of antibody and lysosomal enzymes, such as rhGALNS, it is unlikely that an anti-LE antibody would directly inhibit enzymatic activity. However, the potential to neutralize cellular uptake exists and would interfere with the efficacy of enzyme therapy. Here, the goal was to develop an assay to detect neutralizing factors, such as antibodies, directed against a lysosomal enzyme (LE) administered as part of an enzyme replacement therapy in a patient in which the antibodies or factors from the patient retain their ability to bind LE under physiological conditions.

In addition to LE-specific antibodies, other factors such as free mannose-6-phosphate, IGF2, or soluble CIMPR can interfere with LE uptake. The neutralizing capacity of these factors would also be detected in the screening method.

In various embodiments, removal of interfering substances can be accomplished by isolating the antibody fraction from the serum matrix through an affinity separation under conditions that allow maximal recovery of antibodies with LE-binding activity. In one embodiment, this is accomplished by using a resin conjugated to Protein A/G. In alternative embodiments, removal of interfering substances can be accomplished using a resin conjugated to other proteins or combinations of proteins with Ig domain binding characteristics, including, but not limited to, Protein A, Protein L, Protein A/L and Protein G/L. Conditions are identified that allow formation of antibody-LE complexes under which the LE retains enzyme activity. In various embodiments, the serum is used without alteration.

Methods for purifying LE-specific antibodies are disclosed in U.S. Pat. No. 7,713,709, hereby incorporated by reference. The assay can be used to detect LE neutralizing antibodies or other factors in a body fluid or tissue sample from a subject. In a preferred embodiment, the body fluid is serum.

A preincubation step with LE allows for neutralizing factor-LE complexes to form before exposure to the cells expressing the CI-MPR.

In various embodiments, the disclosure provides a method for detecting lysosomal enzyme (LE)-specific neutralizing factors in a subject comprising: (a) contacting a body fluid sample from the subject with a lysosomal enzyme conjugated to a detection moiety to detect LE-specific neutralizing factors in the body fluid sample, wherein the LE-specific neutralizing factor and lysosomal enzyme detection moiety form a complex; (b) contacting the LE-specific factor/lysosomal enzyme complex from step (a) with cells comprising a cation independent mannose-6-phosphate receptor (CI-MPR), and (c) detecting the presence of LE-specific neutralizing factor in the body fluid sample by detecting the presence of the lysosomal enzyme labeled with the detection moiety inside the cell or on the surface of the cell.

The disclosure also provides a method for determining the presence of lysosomal enzyme (LE)-specific neutralizing factors in a subject comprising the steps of: (a) contacting a body fluid sample from the subject with a lysosomal enzyme conjugated to a detection moiety to detect LE-specific neutralizing factors in the body fluid sample, wherein the LE-specific neutralizing factor and lysosomal enzyme detection moiety form a complex; (b) contacting the LE-specific neutralizing factor/lysosomal enzyme from step (a) with cells comprising a cation independent mannose-6-phosphate receptor (CI-MPR), and (c) detecting the presence of LE-specific neutralizing factor from the body fluid sample by detecting the lysosomal enzyme labeled with the detection moiety inside the cell or on the surface of the cell, wherein a low amount of detectable LE-detection moiety is indicative of the presence of LE-specific neutralizing factors in the sample.

In another aspect, the disclosure provides a method for determining the percent inhibition of lysosomal enzyme activity by lysosomal enzyme (LE)-specific neutralizing factors in a subject comprising the steps of: (a) contacting a body fluid sample from the subject with LE-conjugated magnetic beads; (b) contacting the body fluid sample/LE-bead combination from step (a) with a composition comprising the lysosomal enzyme conjugated to a detection moiety to detect LE-specific neutralizing factors; (c) contacting the combination of (a) and (b) with cells comprising a cation independent mannose-6-phosphate receptor (CI-MPR), and (d) detecting the presence of an LE-specific neutralizing factor from the combination of (a), (b) and (c) and comparing the levels of captured LE-specific neutralizing factor to a control sample with a known amount of LE-specific neutralizing antibody in order to determine the percent inhibition of LE activity and/or titer of neutralizing factors in the body fluid sample.

During the detection step, the levels of LE-specific neutralizing factor in the body fluid sample are determined by detecting the presence of the lysosomal enzyme labeled with the fluorophore (or other detection moiety) inside the cell or on the surface of the cell. A reduced level of detection in the presence of the body fluid sample compared to control indicates that the body fluid sample contains a neutralizing factor that inhibits LE uptake.

During the method, it is contemplated that the body fluid sample and lysosomal enzyme-fluorophore conjugate are contacted together in the same solution. It is also contemplated that the body fluid sample, lysosomal enzyme-bead conjugate and lysosomal enzyme-fluorophore conjugate are contacted together in the same solution. In various embodiments, contacting of the samples is carried out prior to contacting the agents with cells. In one embodiment, all the components may be cultured together in the same mixture with the cells, beginning simultaneously.

In various embodiments, the body fluid sample and lysosomal enzyme-detection moiety conjugate are contacted together for at least about 4 to 8 hours, e.g., 6 hours, prior to contacting with cells. In various embodiments, the body fluid sample, lysosomal enzyme-bead conjugate and lysosomal enzyme-detection moiety conjugate are contacted together for at least about 4 to 8 hours, e.g., 6 hours, prior to contacting with cells. In various embodiments, the contacting can be for about 4, 5, 6, 7, 8, 9, 10, 11 or 12 hours.

In various embodiments, the body fluid sample is contacted with the LE-detection moiety conjugate for at least about six hours. In various embodiments, the contacting can be for at least about 6, 7, 8, 9, 10, 11 or 12 hours. In various embodiments, the contacting is between about 2° and 8° C. In various embodiments, the contacting is at about 4° C. In various embodiments, the body fluid sample and LE-detection moiety are contacted for at least about six hours at approximately 4° C.

In various embodiments, the body fluid sample, lysosomal enzyme-bead conjugate and lysosomal enzyme-detection moiety are contacted with the cells for about three hours. In various embodiments, the body fluid sample and lysosomal enzyme-detection moiety are contacted with the cells for about three hours. In various embodiments, the contacting with cells can be for about 3, 4, 5 or 6 hours. In various embodiments, the contacting with cells is for about 3, 3.25, 3.5, 3.75 or 4 hours. In various embodiments, contacting with cells is between about 34° and 39° C. In various embodiments, the contacting with cells is at about 37° C.

The following Examples are informational and should not be considered limiting.

EXAMPLE 1

Development of Cell-Based Assay to Detect LE-Specific Neutralizing Factors

To evaluate the impact of neutralizing factors, such as neutralizing antibodies, on lysosomal enzyme uptake through CI-MPR, a cell-based flow cytometry assay was developed for detecting factors that neutralize uptake of lysosomal enzymes that may develop when the enzyme is administered as enzyme replacement therapy in patients.

The assay was developed using uptake analysis of rhGALNS, known commercially as VIMIZIM® (elosulfase alfa), but it is contemplated the assay is useful for any lysosomal enzyme that it taken up into cells via the CI-MPR.

Cell uptake of rhGALNS is measured using flow cytometry to determine the amount of fluorophore-conjugated rhGALNS taken up by Jurkat cells. Jurkat cells are a non-adherent human T cell line that express CI-MPR, which binds and targets rhGALNS to the lysosome. rhGALNS neutralizing antibodies (NAb) are detected in samples by a decrease in fluorophore-conjugated rhGALNS uptake (calculated as % inhibition) that exceeds the screening cut point (SCP).

The rhGALNS NAb assay consists of three assay procedures. The screening assay procedure identifies serum samples that contain rhGALNS-neutralizing activity based on assay signals at or above the SCP (inhibition of rhGALNS uptake). The confirmatory procedure determines whether neutralizing activity observed in the screening assay is the result of antibodies by comparing the assay signals of samples with and without removal of antibodies. Depletion of antibodies using rhGALNS coupled to beads is expected to restore rhGALNS uptake. Samples with a change in recovery ratio greater than or equal to the confirmatory cut-point (CCP) are confirmed NAb positive. The titer assay procedure determines the relative potency of neutralizing antibody in each sample by serially diluting positive samples and determining the point at which diluted sample crosses the titer cut-point (TCP).

Screening Assay: For the screening assay, Jurkat T cells were plated at 75,000 cells/well (100 uL) in a 96-well plate tissue culture plate (Fisher) in RPMI-1640 complete media (RPMI-1640 High Glucose, 10% FBS, PSG (100 I.U./mL Penicillin, 100 IU/mL Streptomycin, 0.29 mg/mL L-Glutamine) and incubated 12 hours to overnight at 35-39° C. Patient samples and control samples [anti-rhGALNS (20 µg/mL), anti-rhGALNS (3 µg/mL)] were diluted 1:2.5 in RPMI-1640 serum-free media (RPMI-1640 High Glucose, PSG (100 I.U./mL Penicillin, 100 I.U./mL Streptomycin, 0.29 mg/mL L-Glutamine)) prior to addition to the cells.

Confirmation Assay: For the confirmation assay, rhGALNS-conjugated tosyl-activated magnetic beads were magnetized for 2 minutes, the storage solution decanted and the beads resuspended in 6 mL of Coupling Buffer [1× Dulbecco's phosphate buffered saline (DPBS), 0.01% Tween]. This step was repeated three more times for a total of four washes and the beads plated 100 µL per well into Nunc Round bottom 96-well polypropylene plate. The beads were pulled to the side of the wells with Dynamag 96 side skirted magnet and the coupling buffer removed from wells with multichannel pipette and the skirted magnet also removed. 140 µL per well of previously diluted confirmation QC/sample was added directly to dry beads and the plate shaken on a plate shaker for 60 mins at 800 rpm. Samples may be diluted 1:2.5 in serum-free RPMI-1640 were added to the wells with the beads. The plates were removed from shaker and beads pulled to the side of the wells with Dynamag 96 side skirted magnet. 60 µL per well of all samples were transferred to the assay plate for contacting with Alexa488-conjugated rhGALNS.

Sample Incubation with Alexa488-conjugated rhGALNS: Alexa488-conjugated rhGALNS (stock concentration=1 mg/mL) was diluted with RPMI-1640 Serum-Free Media to a final concentration of 0.4 µg/mL by adding 4.8 µL of Alexa488-conjugated rhGALNS stock to 11995.2 µL RPMI-1640 Serum-Free Media. In a costar 96-well flat bottom plate, 60 µL per well of 0.4 µg/mL Alexa488-conjugated rhGALNS was added in RPMI-1640 Serum-Free Media to all wells as appropriate. For a 1:1 dilution, 60 µL per well of controls were added in duplicate or in quadruplicate for 2 sets into the appropriate wells. Similarly, for a 1:1 dilution of sample, 60 µL per well of patient screening samples were added into the appropriate wells. For a 1:1 dilution for the confirmation assay, 60 µL per well of patient confirmation samples were added in duplicate into the corresponding wells. The plate was covered, wrapped in foil and allowed to incubate overnight for 14 to 20 hours at 2-8° C.

Assay: Prior to the sample incubation step, the cell plates were removed from the $CO_2$ incubator and observed to ensure the cells were healthy and viable. Control and patient samples prepared on for the screening or confirmation assays and stained with the LE-fluorophore conjugate were removed from 2 to 8° C. and placed in $CO_2$ incubator at 35 to 39° C. for 10 to 20 minutes to warm up. 100 µL of samples was added to the cells and the cell plate with samples was placed back into the $CO_2$ incubator at 35 to 39° C. for 3 to 3.5 hours. After the incubation was completed, the cells were washed in PBS by centrifuging the plate for 6 min at 310×g in a tabletop centrifuge at 14 to 18° C., repeated two to five times as appropriate. After the last wash, the plate was removed from the centrifuge, the cell pellet resuspended in 100 µL viability stain (red fluorescent reactive dye 1:1000 dilution) and tested for viability. Once viability testing was complete, the cells were centrifuged 6 min at 310×g in a tabletop centrifuge at 14 to 18° C.

Optionally, the cells are fixed in 1% paraformaldehyde solution (PFA). 100 µL of 1% PFA is added to the cell pellet and vortexed lightly to mix. The fixed cells are covered and stored at 2 to 8° C. for up to 3 days prior to analysis by flow cytometry. Prior to analysis, 50 µL PBS was dispensed to each well to bring the volume in each well up to 150 µL.

The cells may also be analyzed without fixation by resuspension in 150 µL after the last wash.

For sample collection, the entire plate samples were acquired by the cytometer, acquiring approximately 10,000 desired events.

All sample duplicates must have a % CV ≤25.0%. Percent Signal Inhibition (% SI) is calculated as [% SI=1—mean median fluorescence intensity (MFI) of sample/mean MFI of control×100]. Confirmatory assay data were analyzed as recovery ratio, defined as mean confirmatory assay MFI of sample/mean screening assay MFI of sample. The titer was calculated as the interpolated dilution factor at which the sample crossed the titer cut point determined by linear regression analysis (Microsoft Excel). Other statistics are calculated using a t-test, for controls t-statistic for 99% CI=2.66.

A positive control polyclonal goat anti-rhGALNS antibody that neutralized uptake was detectable at concentrations ≥0.97 µg/mL. Assay precision, selectivity, drug tolerance and specificity were determined, and cut points were calculated to set criteria for assessing positive samples.

Confirmation Cut-Point: A fixed CCP was established and used to identify confirmed positive samples. The recovery ratio values for six runs were evaluated for normality in JMP Statistical Software (version 11.0) using box plot analysis. Following the removal of the minimum number of outliers from the data set, analysis of recovery ratio values for each of the six runs determined that all runs were normally distributed (p-value≥0.05, Appendix 3). Pooled variance was then used to calculate the fixed confirmatory cut-point based on the $99^{th}$ percentile of the normal distribution model of the data (Table 4), resulting in a recovery ratio CCP of 1.24. Thus, samples that screen positive and have a recovery ratio ≥1.24 in the confirmatory assay are considered confirmed positive during sample testing.

Screening and Titer Cut-Points: JMP software was used to analyze the normality of the distribution of naïve individual serum screening assay data collected during validation. The sample % SI data distribution was analyzed for normality. Outliers were excluded conservatively by removing the minimum number required to achieve a normal distribution for each run. Pooled variance was then used to calculate the screening cut-point based on the $95^{th}$ percentile and a titer cut-point based on $99.9^{th}$ percentile of the normal distribution model of the data, resulting in a % SI Screening Cut-Point and Titer Cut-Point of 14.02% and 25.76%, respectively. Thus, samples with % SI ≥14.02% in the screening assay are considered positive during sample testing.

Drug Tolerance (rhGALNS Drug Interference): Drug tolerance was evaluated using Normal Human Pooled Serum (NHPS) spiked with 3 µg/mL (Low Positive, LP) or 20 µg/mL (High Positive, HP) of the positive control anti-rhGALNS antibody. Samples containing positive control concentrations as described above were dosed with either 0 µg/mL of rhGALNS or one of seven concentrations of rhGALNS drug (2.00 µg/mL, 0.67 µg/mL, 0.22 µg/mL, 0.074 µg/mL, 0.025 µg/mL, 0.008 µg/mL and 0.0027 µg/mL). All samples were assayed per the screening method on a single plate by one analyst. The highest neat concentration of rhGALNS at which the low and high PC-spiked samples screened positive was 2.00 µg/mL, the highest concentration tested. The increase in % SI of the NHPS and Low Positive-spiked sample at 2.0 µg/mL may indicate competitive uptake inhibition of the unlabeled with the Alexa 488-conjugated rhGALNS drug. These data suggest that the assay can tolerate up to 0.22 µg/mL rhGALNS drug before it interferes with uptake of the Alexa 488-conjugated rhGALNS drug. It is recommended to minimize drug interference by collecting samples just prior to weekly or every other week dosing.

rhGALNS NAb assay was validated and ready for implementation within clinical testing. Clinical samples generating % SI results ≥14.02 are deemed presumptive positives and require confirmation testing. In confirmation testing, samples are immunodepleted with 30 mg/mL of rhGALNS coupled Tosyl-Activated Dynabeads. Samples with a recovery ratio ≥ the CCP of 1.24 are reported as positive for the presence of rhGALNS-specific neutralizing antibodies. Positive samples are tested using the titer assay to determine the level of anti-rhGALNS neutralizing antibodies using a % SI titer cut point of 25.76%.

Confocal Imaging: Internalization of Alexa488-rhGALNS and trafficking to lysosomes was confirmed by confocal microscopy by incubating cells from the functional NAb assay described in section 2.3 with 50 nM LysoTracker Red (Molecular Probes) at 37° C. for 1 h. Cells were then washed with serum-free RPMI-1640 and mounted with Prolong Gold Antifade Mountant with DAPI (Molecular Probes), sealed, and visualized using a Leica SP8 confocal microscope (Leica Microsystems). Confocal Z-stacks were acquired using a 63× Plan-Apo objective with 4× zoom and LASX software (Leica Microsystems). Z-stacks were rendered in 3-D and exported using Volocity software version 6.3 (PerkinElmer).

Detection of Human Anti-rhGALNS Antibodies from Serum

The principle of the assay is to measure the internalized fluorophore labeled drug. In this case, the presence of a positive AlexaFluor488 signal indicates the absence of neutralizing antibodies within the patient sample, thus, allowing the internalization of the AlexaFluor488 labeled drug into the cell. The absence of an AlexaFluor488 signal indicates the presence of neutralizing antibodies or other neutralizing factors within the patient sample, thus, blocking the internalization of the AlexaFluor488 labeled drug.

After carrying out the above screening and confirmation assays to determine the amount of rhGALNS NAb in a patient sample, is was determined that Jurkat T cells expressing CI-MPR on the cell surface internalized Alexa488-labeled rhGALNS with a $K_{uptake}$ of approximately 5 µg/mL after 4 hours incubation at 37° C. Experiments with Trypan Blue quenching, incubation of cells with Alexa488-rhGALNS at 4° C. instead of 37° C., or treatment of cells with Cytochalasin D, indicated that the MFI signal measured by the flow cytometer resulted from internalized Alexa488-rhGALNS and not Alexa488-rhGALNS bound to the cell surface.

Comparison of assay parameters from the validated cell uptake NAb assay and in vitro receptor binding NAb assays was performed. Re-testing of ~800 subject samples from a Phase 3 study showed 89% of sample results from both assays are concordant for NAb incidence across all time points and treatment groups.

Figure 2A:
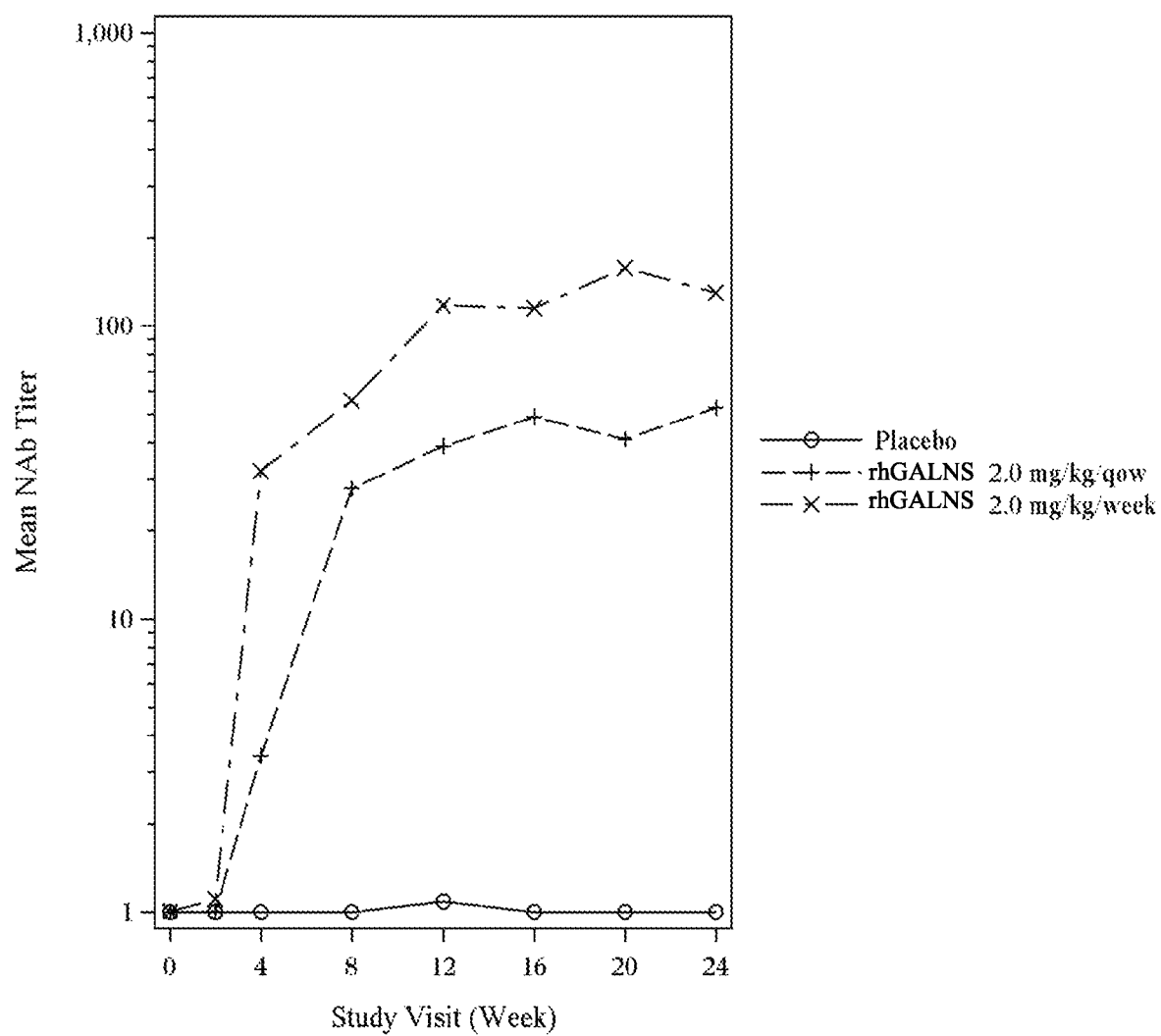
FIGS. 2A and 2B show that antibodies to infused rhGALNS (elosulfase alfa) were detectable in patient serum. Positive samples (FIG. 2A) show comparatively low NAb titers relative to anti-rhGALNS total antibody (TAb) titers (FIG. 2B).
Figure 2B:
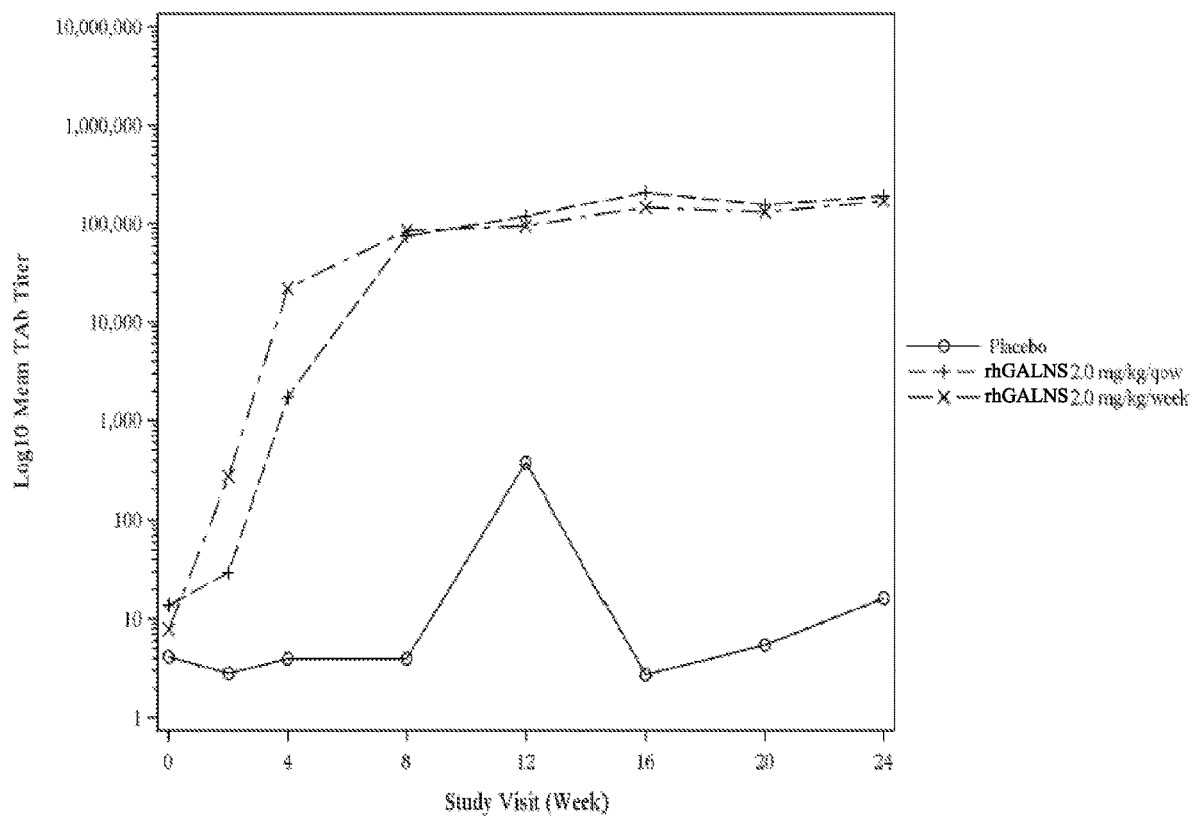

Samples from a 24 week study of rhGALNS (elosulfase alfa) treatment were assessed for NAb at baseline and weeks 2, 4, 8, 12, 16, 20 and 24. rhGALNS was infused at 2.0 mg/kg body weight in two dosing cohorts, weekly and every other week (QOW). Positive samples (FIG. 2A) show comparatively low NAb titers [wk 24 mean 52 (range 0 to 1,098) in the weekly group and 130 (range 0 to 1,659) in the QOW group] relative to anti-rhGALNS total antibody (TAb) titers [wk 24 mean 167,737 (range 0 to $1.77 \times 10^6$) in the weekly group and 190,901 (range 810 to $1.77 \times 10^6$) in the QOW group] (FIG. 2B).

These results show this cell-based flow cytometry assay detects neutralizing antibodies, or other factors, to rhGALNS and this platform is applicable to detection of neutralizing antibodies and other neutralizing factors to other enzyme replacement therapy enzymes that undergo receptor-mediated internalization.

EXAMPLE 2

Detection of Neutralizing Factors that Block Lysosomal Enzyme Uptake into Cells

Figure 3A:
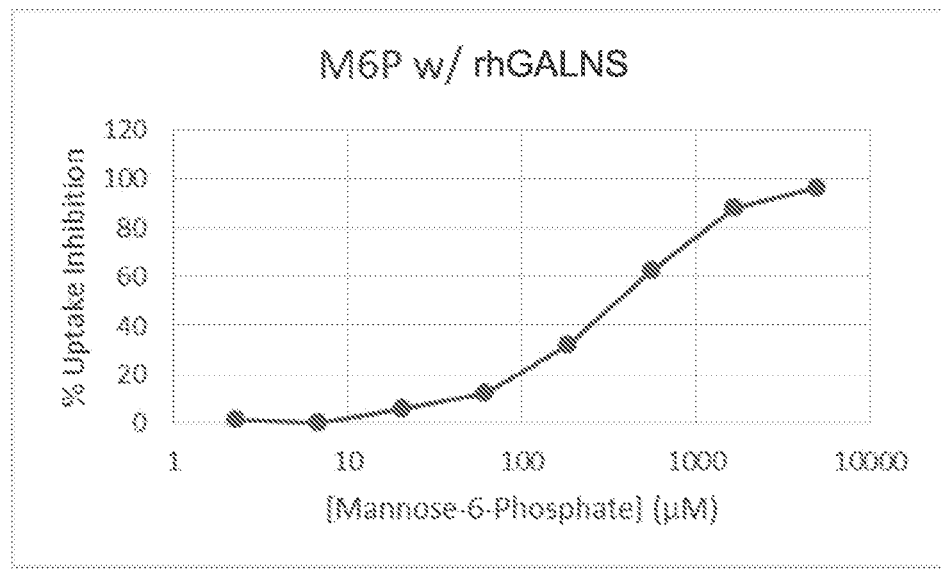
FIGS. 3A-3C show that M6P has a dose dependent effect at inhibiting rhGALNS uptake into Jurkat cells (FIG. 3A) while IGF-II only shows partial inhibition of rhGALNS uptake (FIG. 3B). Soluble CI-MPR also inhibits rhGALNS uptake (FIG. 3C).
Figure 3B:
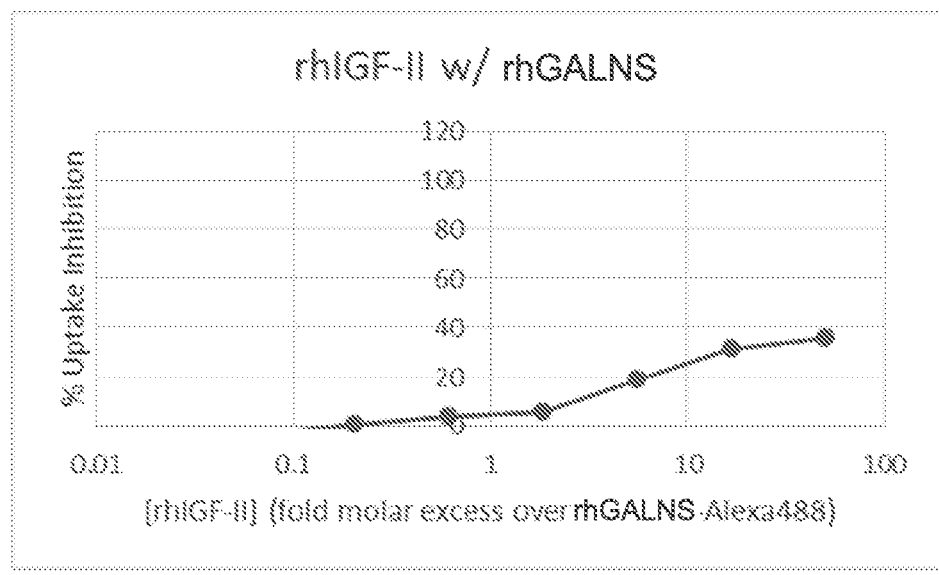
Figure 3C:
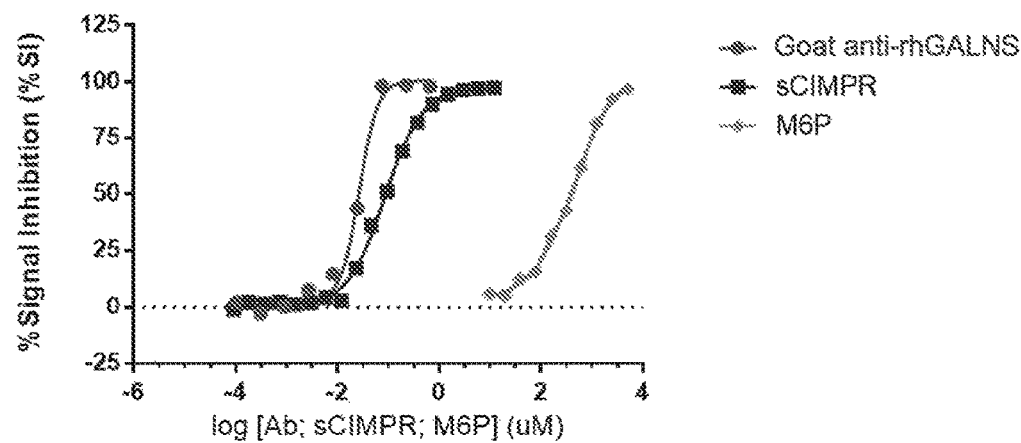

The ability of other factors that bind to the CI-MPR to inhibit uptake of rhGALNS in the assays was also measured. rhGALNS binds to the CI-MPR via mannose 6 phosphate on the protein. Other possible neutralizing factors such as free M6P, IGF-II and soluble CI-MPR were incubated in the assay in the place of neutralizing antibodies. Results of the assay showed that culture of the cells in the presence of M6P has a dose dependent effect at inhibiting rhGALNS uptake into Jurkat cells, with 0.5M M6P exhibiting approximately 32% inhibition of rhGALNS uptake and 5M M6P exhibiting approximately 96% inhibition (FIG. 3A). In contrast, IGF-II, only shows partial inhibition of rhGALNS uptake (FIG. 3B). Soluble CI-MPR, isolated from bovine serum, also functionally inhibited uptake of rhGALNS by competing for binding to cellular CI-MPR on the Jurkat cells in a concentration-dependent manner (FIG. 3C).

These results show that mannose-6-phosphate directed cellular uptake of LEs can be specifically blocked by excess soluble mannose-6-phosphate and by soluble receptor (sCI-MPR) in the method.

The assay was also validated for a CI-MPR ligand that is not mannose-6 phosphate. The ability of CI-MPR expressing Jurkat or HepG2 cells were analyzed by flow cytometry for their ability to take up labeled GAA comprising an IGF-II tag, which facilitates binding to the CI-MPR. Both Jurkat and HepG2 cells were able to internalize GAA-IGFII as determined by intracellular fluorescence signal. This uptake was inhibited by unlabeled GAA as well as anti-IGFII antibody.

Figure 4A:
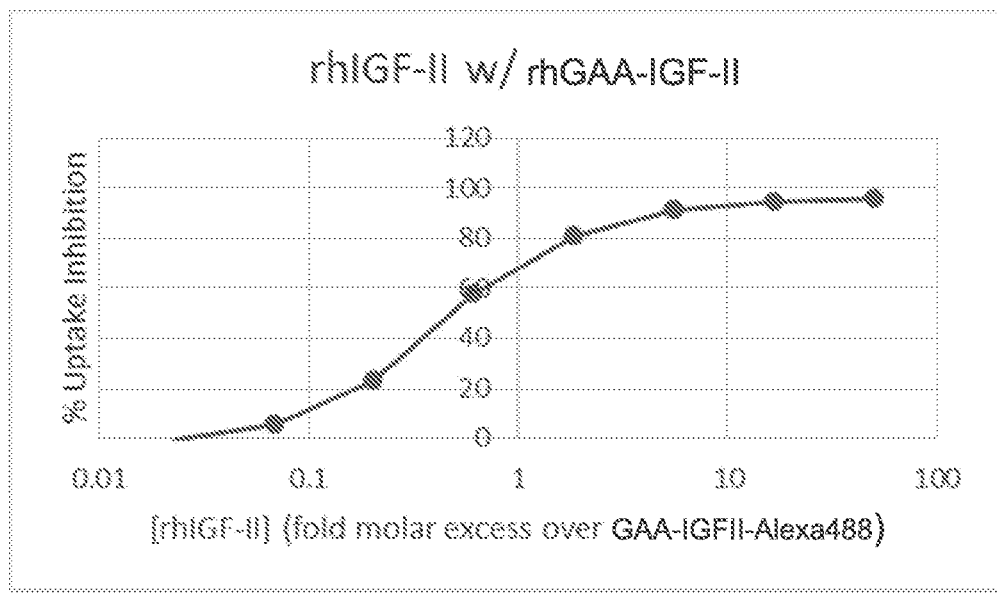
FIGS. 4A-4B show that IGF-II has a dose dependent effect at inhibiting rhGAA-IGF-II uptake into Jurkat cells (FIG. 4A) while M6P only shows partial inhibition of rhGAA-IGF-II uptake (FIG. 4B).
Figure 4B:
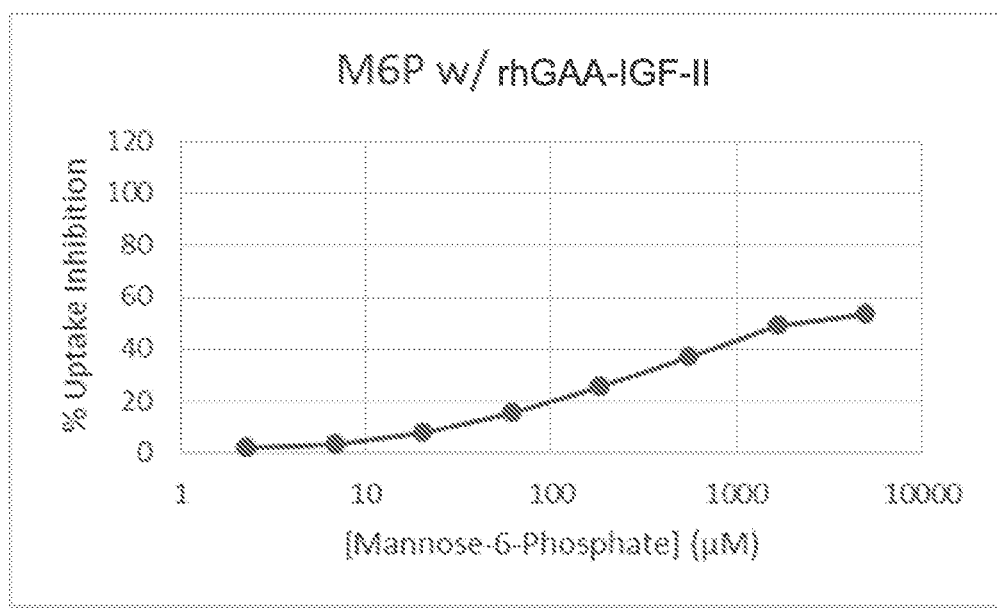

Results of the assay showed that culture of the cells in the presence of IGF-II has a dose dependent effect at inhibiting rhGAA-IGF-II uptake into Jurkat cells, with 0.6M excess IGF-II exhibiting approximately 58% inhibition of rhGALNS uptake and 50M excess IGF-II exhibiting approximately 95% inhibition (FIG. 4A). In contrast, M6P only shows partial inhibition of rhGAA-IGF-II uptake (FIG. 4B).

These results show that Glycosylation Independent Lysosomal Targeting can be specifically blocked by excess IGF-II in the method.

EXAMPLE 3

Additional Functional NAb Assay Development

In additional analysis, the flow cytometry gating strategy restricted MFI analysis to single, live Jurkat cells for measurement of Alexa488-rhGALNS uptake. To assess optimal rhGALNS uptake conditions by Jurkat cells in vitro, an Alexa488-rhGALNS dose-response curve was generated (0 to 363.6 nM or 0 to 40 µg/ml). A dose-dependent increase in MFI was observed in Jurkat cells incubated with Alexa488-rhGALNS, with a background of untreated cells detected at an MFI of 43.7±4.7 ($K_{uptake}$=46.3 nM by Hanes-Woolf plot linear regression analysis; FIGS. 5A and B).

To determine if the MFI signal detected after incubation of cells with Alexa488-rhGALNS resulted from internalized drug or drug bound to the cell surface, a series of experiments was conducted whereby cells incubated with Alexa488-rhGALNS (0.4 µg/mL) in the presence of 20% pooled human serum were either placed at 4° C., quenched with trypan blue, or treated with cytochalasin B. Cells incubated at 4° C., which allowed for drug binding but not uptake, produced an MFI of 92.9±1.50 compared with an MFI of 4425±98.6 when cells were incubated for the same length of time at 37° C. (FIG. 5C), suggesting that MFI predominantly measured internalization of Alexa488-rhGALNS. Next, cells post-incubation with Alexa488-rhGALNS were treated with trypan blue, which is impermeable to vital cells, quenches Alexa488 fluorescence [Sahlin, et al., J. Immunol. Methods 60 (1983) 115-124], and was expected to reduce MFI signals if Alexa488-rhGALNS was bound to the cell surface. As a control to ensure that trypan blue quenched Alexa488 on the surface of Jurkat cells, cells were labeled with an Alexa488-conjugated mouse monoclonal antibody (Clone SP34-2) that binds CD3 expressed on the cell surface of T cells [Osman et al., Eur. J. Immunol. 22 (1992) 2995-3000]. Increasing concentrations of trypan blue reduced the fluorescence of cells treated with Alexa488-labeled anti-CD3 (FIG. 5D). However, concentrations of trypan blue up to 0.4% had no impact on Alexa488-rhGALNS MFI values, suggesting that almost all of the MFI signal emitted from Alexa488-rhGALNS-treated cells was the result of drug internalization within cells (FIGS. 5C and D). To determine whether drug internalization was a result of endocytosis, cells were pretreated with cytochalasin B for 1 hour prior to incubation with Alexa488-rhGALNS. MFI signal emitted from Alexa488-rhGALNS-treated cells was reduced to 777±4.2 MFI in the presence of 374 µM cytochalasin B (FIG. 5C).

To confirm the uptake mechanism of Alexa488-rhGALNS via CI-M6PR, cells were incubated with Alexa488-rhGALNS in the presence of excess soluble CI-M6PR (sCI-M6PR) or M6P to compete for CI-M6PR binding sites, or an affinity-purified goat anti-rhGALNS polyclonal antibody to neutralize rhGALNS binding. Increasing concentrations of sCI-M6PR, M6P, and anti-rhGALNS antibody dose dependently abrogated Alexa488-rhGALNS uptake ($IC_{50}$ [µM]=0.085 for sCI-M6PR, 452.9 for M6P, and 0.027 for anti-rhGALNS; FIG. 5E). $IC_{50}$ values for M6P were higher than those for sCI-M6PR or anti-rhGALNS, likely due to competition with multiple M6P moieties on rhGALNS and additional proteins containing M6P binding sites. Furthermore, confocal imaging of Alexa488-rhGALNS-treated cells revealed that Alexa488-rhGALNS co-localized with lysosomes, confirming that labeled rhGALNS is efficiently internalized and trafficked to the lysosomes. Collectively, these data indicate that internalization of Alexa488-rhGALNS occurs through M6P-mediated receptor binding to CI-M6PR followed by endocytosis and trafficking to the lysosome.

Figure 6A:
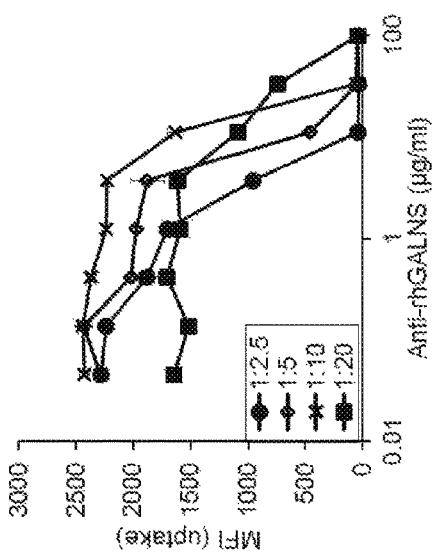
FIGS. 6A-6C show determination of optimal Alexa488-rhGALNS concentration for detection of inhibitory antibodies.
Figure 6B:
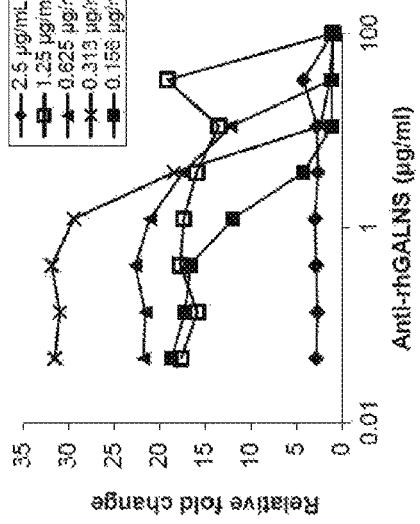

Determination of Optimal Alexa488-rhGALNS Concentration and Serum Dilution for Detection of Inhibitory Antibodies A series of dose-response curves was generated to determine the optimal drug dose that would provide detection of approximately 1 µg/mL affinity-purified goat anti-rhGALNS polyclonal antibody positive control (AbPC) in the presence of 20% pooled human serum. Alexa488-rhGALNS was added to cell media at a final concentration of 0.156 µg/mL to 2.50 µg/mL in the presence of increasing concentrations of AbPC ranging from 0.046 to 100 µg/mL. AbPC interfered with uptake of Alexa488-rhGALNS in a dose-dependent manner (FIG. 6A). These data were then transformed and plotted as the relative fold change over the maximum concentration of AbPC tested (100 µg/mL; FIG. 6B) to determine the dose of Alexa488-rhGALNS that would provide a sensitivity of approximately 1 µg/mL for AbPC. A concentration of 0.313 µg/mL Alexa488-rhGALNS gave the highest signal-to-noise ratio, and an approximate maximal SI of 92% was observed in the presence of 11.1 µg/mL AbPC. Together, these data led to the selection of 0.4 µg/mL Alexa488-rhGALNS for further assay development, including the assay sensitivity analyses described below.

Figure 6C:
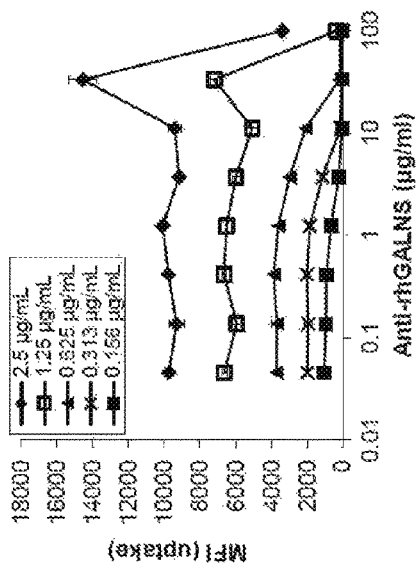

To characterize the potential effect of interference from serum components (matrix interference) on detection of NAbs, NPS samples spiked with AbPC at concentrations ranging from 0.046 to 100 µg/mL were diluted 2.5-, 5-, 10-, and 20-fold in serum-free media and mixed 1:1 with 0.4 µg/mL Alexa488-rhGALNS. A dilution of 1:2.5 (equivalent to 20% pooled human serum after mixing with Alexa488-rhGALNS) showed inhibition of Alexa488-rhGALNS uptake at <1 µg/mL and inhibited uptake at the lowest AbPC concentration relative to the other dilutions (FIG. 6C). The 1:20 dilution reduced detection of Alexa488-rhGALNS, even in the absence of inhibition by AbPC (FIG. 6C), which indicated that low NPS concentrations can independently reduce drug uptake in this assay. Therefore, a minimum required dilution (MRD) of 1:2.5 was chosen to provide optimal sensitivity.

Assay Cut Points for the Cellular Uptake NAb Assay A tiered clinical testing strategy was adopted to screen, confirm, and titer NAb samples that were confirmed positive for binding anti-elosulfase antibodies (also referred to as total anti-elosulfase antibody, TAb) [Mire-Sluis et al., J Immunol. Methods 289 (2004) 1-16]. To define a NAb assay positive/negative cut point, serum was collected from drug-naïve individuals with Morquio A syndrome (n=48) and analyzed in duplicate in 6 separate experiments performed by 2 analysts over 2 days. At the time of assay development, serum was unavailable from individuals with Morquio A syndrome; thus, pooled serum from healthy donors without Morquio A syndrome was used. The sample % SI data distribution for each run was analyzed for normality using the Shapiro-Wilk test (JMP software, SAS Institute Inc). Outliers, identified using box plot analysis (JMP), were excluded conservatively by removing the minimum number required to achieve a normal distribution for each run [Shankar et al., J. Pharm. Biomed. Anal. 48 (2008) 1267-1281]. This approach resulted in normal distributions being established after exclusion of 2 outliers (0.69%) from the total screening data set. Pooled variance was then used to calculate the screening cut point (SCP) based on the 95th percentile to avoid false-negatives responses, resulting in an SCP of 14.02% SI. Thus, individual serum samples that reduced signal by ≥14.02% compared with control serum in the screening step were considered reactive (potentially positive) during sample testing.

For samples that screened as reactive (potentially positive), a confirmation step assessed whether the sample signal was increased by depletion of rhGALNS-specific antibodies, as would be expected of true-positive samples. Drug-conjugated beads were used to deplete rhGALNS-specific antibodies from serum prior to retesting in the cell-based assay. A confirmation cut point (CCP) was established by depleting the same drug-naïve serum samples described above and comparing each with its corresponding non-depleted sample tested on the same plate. A fixed CCP (recovery ratio of immunodepleted sample signal/non-depleted sample signal) was determined by first evaluating results from each run for normality and outliers. Lack of normality was observed in 2 of 6 runs based on the Shapiro-Wilk test (p≤0.05), but the removal of the minimum number of outliers from the data set (n=4 [1.41% of data set]) resulted in a normal distribution for all runs (p≥0.05). Pooled variance was then used to calculate the fixed CCP based on the 99th percentile of the normal distribution model of the data, resulting in a recovery ratio CCP of 1.24. Thus, samples that were reactive in the screening step and had a recovery ratio ≥1.24 in the confirmatory step were considered positive during sample testing.

NAb-positive samples were subsequently 3-fold serially diluted (1:2.5, 1:7.5, 1:22.5, etc.) in a titer experiment to determine relative NAb levels. A titer cut-point (TCP) of 25.76% SI was calculated based on the 99.9th percentile of the normal distribution data model described for the screening step. To extrapolate a titer value, at least 1 dilution of a positive sample had to drop below the TCP.

Once samples from drug-naïve individuals with Morquio A syndrome became available from the clinical trial, the screening and confirmation cut points established during assay validation were verified using raw MFI data from 115 baseline and placebo samples collected from 60 drug-naïve individuals with Morquio A syndrome and tested over 4 months by 4 analysts. Using a similar statistical approach to the one described above for donors without Morquio A syndrome, the target treatment population cut points were comparable to the original cellular uptake NAb assay cut points derived from non-affected individuals (Table 1). For the purpose of a concordance assessment, the cut points of the ELISA-based CI-M6PR binding assay previously used to detect anti-elosulfase alfa NAb [Schweighardt et al., Clin.Ther. 37 (2015) 1012-1021.e6] were also confirmed in the 115 baseline and placebo samples (Table 1). NAb assay concordance using the cut points from Morquio A individuals was 90%, supporting the use of cut points established with non-affected individuals in the validated assay.

TABLE 1

| Cut Point Type | Normal Serum | | Morquio A Serum | |
|---|---|---|---|---|
| | Cell-based Assay | Ligand-based Assay | Cell-based Assay | Ligand-based Assay |
| SCP (% SI) | 14.0 | 14.8 | 19.6 | 22.8 |
| CCP (Recovery Ratio) | 1.24 | 1.05 | 1.15 | 1.09 |
| TCP (% SI) | 25.8 | N/A | 30.0 | N/A |

Sensitivity and Precision For detection of neutralizing antibodies elicited by biologic therapies, industry guidelines recommend an assay sensitivity of ≤1 µg/mL positive control antibody [Gupta et al., J. Immunol. Methods 321 (2007) 1-18]. To determine the lowest concentration of antibody that can be detected in the assay (i.e. sensitivity or limit of detection [LOD]), AbPC was spiked into NPS at 20 µg/mL and serially diluted 3-fold to generate an 8-point series (n=18). For each dilution series, values crossed the screening cut point with the % SI signals from at least 2 dilutions ≥SCP and at least 1 dilution <SCP, and the mean neat concentration of AbPC was calculated from the interpolated concentration at the SCP using linear regression analysis and correction for the MRD. The sensitivity and LOD of the assay was determined to be 0.97 µg/ml (FIG. 7A).

Once study samples became available, the sensitivity of the method was confirmed using serum from individuals with Morquio A syndrome prior to treatment with elosulfase alfa. From 6 dilution curves assayed over 3 days by a single analyst, a mean value of 0.30 µg/mL was interpolated at the SCP for samples from individuals with Morquio A (FIG. 7B), a value similar to the 0.97 µg/mL value obtained during assay validation using NPS (FIG. 7A).

Assay precision describes the closeness of replicate measurements of the same sample on the same plate (intra-assay) or between plates (inter-assay). QC concentrations were selected to assess assay precision and monitor the assay performance in the presence of high and low concentrations of NAb. AbPC spiked into NPS at 20 µg/mL and 3 µg/mL were chosen as high quality control [HQC] and low quality control [LQC] concentrations, respectively, based on AbPC performance when serially diluted (FIG. 7A). To evaluate assay precision, AbPC was spiked into NPS at 20 µg/mL (HQC and titer quality control [TQC] concentrations), 3 µg/mL (LQC concentration) or unspiked (negative quality control [NQC] concentration) and the intra-assay and inter-assay coefficient of variation (CV) was assessed. An example of the raw histogram data for each of these QC samples is presented in FIG. 7C. The intra- and inter-assay precision was 0.60% and 0.65% CV for the HQC, 12.02% and 17.62% CV for the LQC, 14.88% and 16.50% CV for the NQC, and 12.41% and 28.04% CV for LQC samples that were confirmed (Table 2). Intra-batch n values vary slightly between QCs due to differences in the number of QCs tested on each plate and exclusion of several samples due to instrument malfunction. Titration of TQC samples showed that 14 of 18 results were within ±one 3-fold dilution of the median interpolated dilution of 28.54.

with LQC screened positive/reactive, suggesting that hemolysis does not interfere with the detection of anti-rhGALNS.

Assay selectivity was confirmed in drug-naïve baseline samples from the clinical study. Selectivity was performed in 10 individual samples by adding AbPC to the LQC concentration in an aliquot of each sample. These spiked baseline samples, as well as the corresponding unspiked serum, were assayed together on a single plate. No matrix interference was observed using either the healthy or target

TABLE 2

|  | Intra-batch (within run) statistics (Pooled) | | | | Inter-batch (between run) statistics (ANOVA) | | | |
| --- | --- | --- | --- | --- | --- | --- | --- | --- |
|  | N (samples) | Average | SD | % CV | N (samples) | Average | SD | % CV |
|  | | % SI | | | | % SI | | |
| HQC | 2.22 | 96.80 | 0.58 | 0.6 | 67 | 96.80 | 0.63 | 0.65 |
| LQC | 2.26 | 60.28 | 7.24 | 12.02 | 68 | 60.74 | 10.71 | 17.62 |
|  | | Median MFI | | | | Median MFI | | |
| NQC | 2.27 | 8654.6 | 1287.6 | 14.88 | 66 | 8691.7 | 1434.0 | 16.5 |
|  | | Recovery ratio | | | | Recovery ratio | | |
| LQC-C | 2.33 | 3.02 | 0.37 | 12.41 | 54 | 3.05 | 0.85 | 28.04 |

Figure 8:
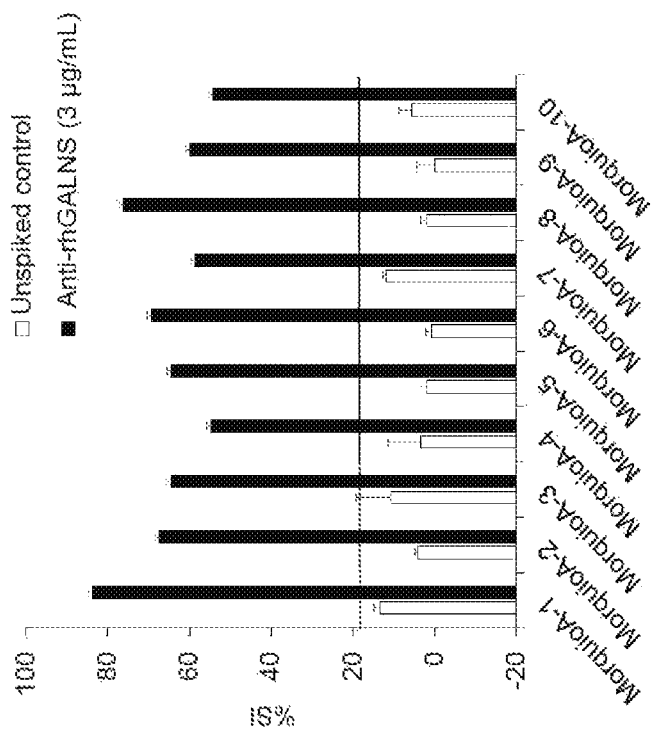
FIGS. 8A-8B represent the interference of matrix on the detection of anti-elosulfase alfa antibodies. % SI data from 5 male and 5 female healthy individual serum samples, as well as 4 lipemic and 4 hemolyzed serum samples, spiked with 3 µg/ml anti-rhGALNS (LQC) or unspiked controls.
Figure 8:
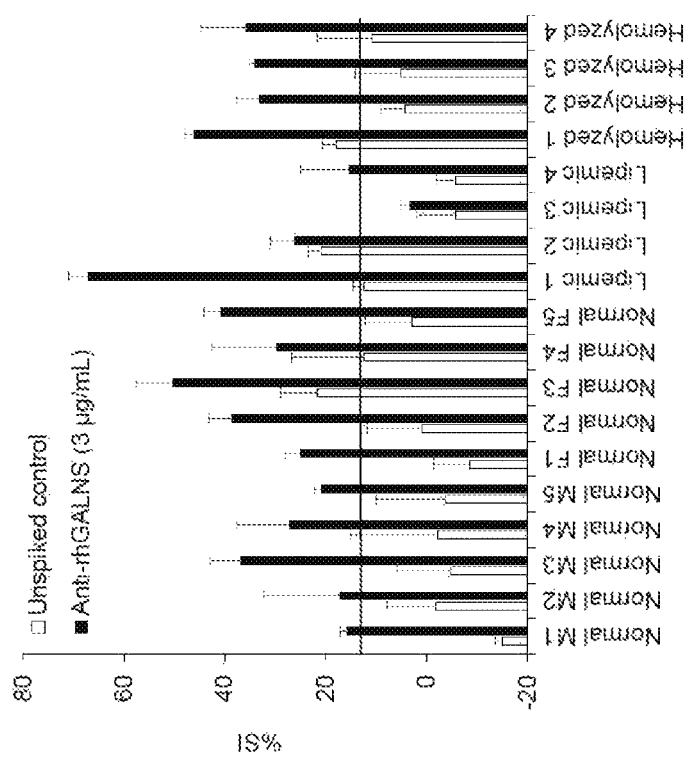

Specificity and Selectivity To evaluate the specificity of rhGALNS neutralization by NAbs in the uptake assay, samples were prepared by spiking both NPS and NPS+LQC AbPC with a non-specific goat IgG-negative control at a concentration of 3 µg/mL. NPS spiked with only non-specific goat IgG antibody tested negative in the screening and confirmatory assays. NPS+LQC AbPC, both with and without non-specific goat IgG antibody, screened and confirmed positive (Table 3), suggesting that the assay is specific for anti-rhGALNS antibodies.

treatment population-based SCP. All 10 unspiked samples (100%) screened negative and all 10 samples (100%) containing LQC AbPC screened positive using the target population-derived SCP (FIG. 8B).

Drug Tolerance The susceptibility of the assay to interference from circulating levels of drug was evaluated using NPS spiked with or without LQC or HQC concentrations of the AbPC in the presence of 0 to 2 µg/mL unlabeled rhGALNS. As expected, LQC and HQC AbPC screened positive in the absence of unlabeled rhGALNS (Table 4).

TABLE 3

|  | LQC | Non-specific IgG | % SI | % CV | Recovery Ratio | Above SCP | Above CCP | Result |
| --- | --- | --- | --- | --- | --- | --- | --- | --- |
| Screening assay | + | + | 25.54 | 4.38 | N/A | Yes | N/A | Positive |
|  | + | − | 31.86 | 9.28 | N/A | Yes | N/A | Positive |
|  | − | + | −6.32 | 9.67 | N/A | No | N/A | Negative |
|  | − | − | −1.02 | 7.18 | N/A | No | N/A | Negative |
| Confirmatory assay | + | + | N/A | 2.04 | 1.42 | N/A | Yes | Positive |
|  | + | − | N/A | 3.46 | 1.55 | N/A | Yes | Positive |
|  | − | + | N/A | 3.87 | 1.05 | N/A | No | Negative |
|  | − | − | N/A | 7.24 | 1.13 | N/A | No | Negative |

To assess effects of serum components on the detection of anti-rhGALNS in this assay, serum from 10 (5 male/5 female) individual donors as well as 4 lipemic and 4 hemolyzed sera from drug-naïve, healthy individuals (without Morquio A syndrome) were tested using the screening assay. To each of these samples, 0 µg/mL (NQC concentration) or 3 µg/mL (LQC concentration), of AbPC was added to evaluate assay selectivity. All normal serum samples (10/10) spiked with LQC were potentially positive/reactive in the screening step (FIG. 8A). Of the 4 lipemic samples spiked with LQC concentration of AbPC, 1 of 4 (25%) screened positive, suggesting that there may be interference from serum lipids in the detection of lower levels of anti-rhGALNS. Conversely, all of the hemolytic samples spiked When low concentrations of unlabeled rhGALNS (≤0.074 µg/mL) were added to LQC or HQC AbPC, the % SIs were comparable to those measured in the absence of unlabeled rhGALNS (Table 4), with slight differences likely due inherent assay variability.

TABLE 4

| Elosulfase alfa (µg/mL) | NHPS (% SI) | LQC (% SI) | HQC (% SI) |
| --- | --- | --- | --- |
| 2.00 | 55.42* | 53.63* | 22.90 |
| 0.67 | 26.94* | 16.72 | 95.08 |
| 0.22 | 8.00 | 23.21 | 95.35 |
| 0.074 | −5.58 | 50.70 | 95.76 |
| 0.025 | −7.21 | 66.34 | 95.47 |

TABLE 4-continued

| Elosulfase alfa (μg/mL) | NHPS (% SI) | LQC (% SI) | HQC (% SI) |
|---|---|---|---|
| 0.008 | 3.79 | 69.97 | 95.26 |
| 0.0027 | −10.84 | 61.71 | 95.26 |
| 0 | −13.25 | 61.34 | 95.02 |

All LQC and HQC AbPC-spiked samples screened positive in the presence of 2 μg/mL unlabeled rhGALNS. However, concentrations ≥0.22 μg/mL of unlabeled rhGALNS reduced Alexa488-rhGALNS uptake in NPS without AbPC. These data suggest that unlabeled rhGALNS inhibited uptake of Alexa488-rhGALNS and indicate that the assay can tolerate up to 0.22 μg/mL rhGALNS introduced via patient serum. Since NAb samples were collected from individuals with Morquio A syndrome just prior to dosing, when elosulfase alfa has been completely cleared [Qi et al., Clin.Pharmacokinet. (2014)], it is unlikely that elosulfase alfa would be present in samples at concentrations sufficient to interfere with the assay.

Figure 9:
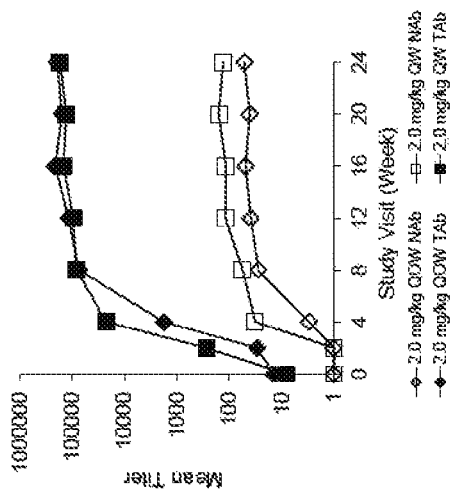
FIGS. 9A-9B show NAb assay concordance and titers in individuals treated with elosulfase alfa in the MOR-004 study.
Figure 9:
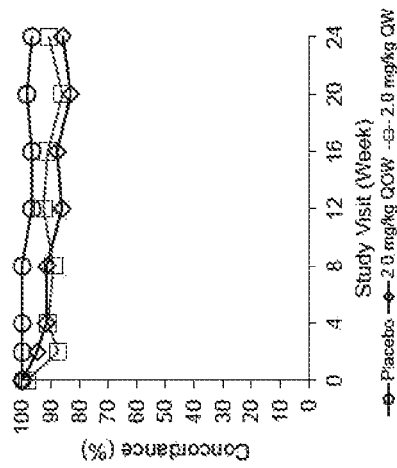

NAb titers and clinical outcomes To compare the functional NAb assay with the previously reported ELISA-based CI-M6PR binding assay for detecting NAb in elosulfase alfa-treated individuals with Morquio A syndrome [Schweighardt et al., supra], serum samples from the clinical trial were reanalyzed with the cell-based assay. Sufficient serum-sample volumes were available for the majority (842/847 [99%]) of serum sample collection time points to obtain confirmed positive/negative results. The overall concordance was high (89%) between NAb positivity in the receptor binding assay and the cell-based assay. Furthermore, the concordance was consistent over the 24-week treatment period (FIG. 9A). Concordance between the assays at each study visit week is presented in FIG. 10.

TAb titers detected using the CI-M6PR binding assay reported previously [Schweighardt et al., supra] were compared to the time course for NAb titer development detected with the functional NAb assay (FIG. 9B). Titers of both TAbs and NAbs increased rapidly during the first 8 weeks of treatment then plateaued from week 8 to week 24 in both the QOW and QW treatment groups (FIG. 9B). Although the frequency of drug administration had minimal effect on TAb and NAb titers at week 24, the QW treatment group appeared to have higher titers of both TAbs and NAbs in the initial 4 weeks of treatment. Subjects in both the QOW and QW treatment groups developed different NAb titer courses over 24 weeks. Titers either initially developed and then remained relatively constant or gradually declined, or showed an intermittent pattern.

EXAMPLE 4

NAb Titers and Efficacy Responses at Week 24

The primary efficacy measure in the clinical study was the distance walked in a 6MWT, which provides a measure of endurance. Keratan sulfate, an rhGALNS substrate, was also measured in individuals' urine (uKS) to track the pharmacodynamic effect of treatment with elosulfase alfa. NAb titers detected with the functional NAb assay were plotted against the change from baseline to week 24 in 6MWT distance, and the percentage change in uKS from baseline. No association was observed between NAb titer and 6MWT (FIG. 11A) or NAb titer and uKS (FIG. 11B) in individuals dosed weekly or every 2 weeks. These data indicate that NAb titers had no detrimental impact on elosulfase alfa efficacy during the 24-week treatment period.

Figure 12A:
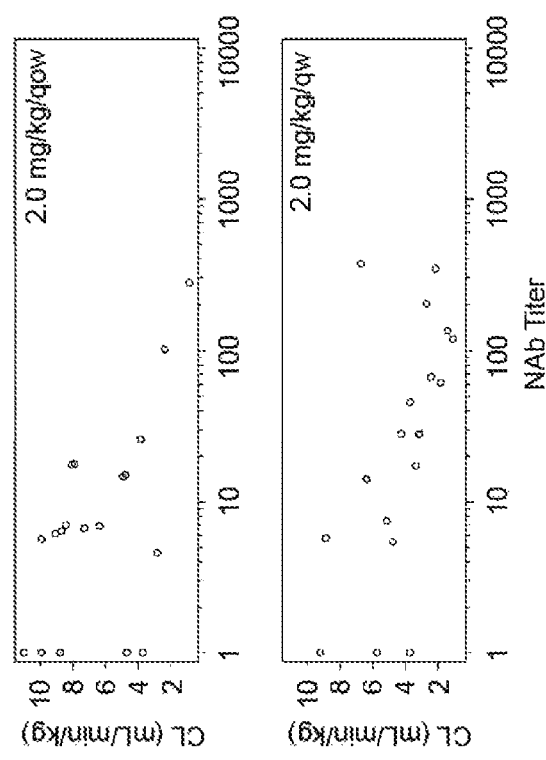
FIGS. 12A-12B show NAb titer correlation with elosulfase alfa half-life and clearance in individuals in the MOR-004 study.
Figure 12B:
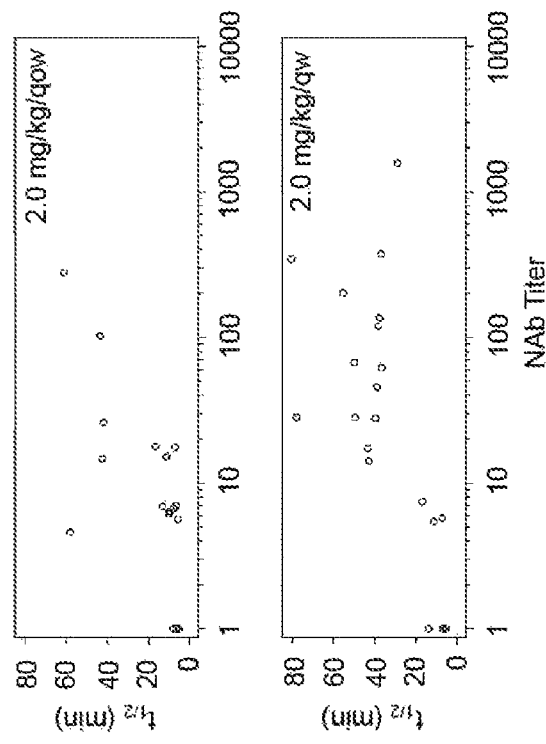

Effect of NAb Titer on Elosulfase Alfa Pharmacokinetics: In order to further explore the association between NAbs and pharmacokinetics, NAb titers from the functional NAb assay were compared to total clearance (CL) of drug after intravenous administration and elimination half-life ($t_{1/2}$). Increased NAb titers were associated with prolonged $t_{1/2}$ in both the QOW and QW cohorts (FIG. 12A). Both cohorts also displayed a trend toward a correlation between increased NAb titers and decreased CL (FIG. 12B). Together these results suggest that NAbs may slow the clearance of elosulfase alfa from plasma.

Summary

Compared with the previously used CI-M6PR binding assay, the format of this cell-based assay measures interference with cellular uptake of elosulfase alfa. This assay format was anticipated to demonstrate greater physiological relevance to the in situ environment due to the interaction of NAb-drug complexes with functional CI-M6PR on living human cells. In contrast, previously reported in vitro CI-M6PR binding assay measures the interaction of biotin-labeled rhGALNS with bovine-derived CI-M6PR immobilized on an ELISA plate [Schweighardt et al., supra]. For the functional NAb assay, human T-cell lymphoma Jurkat cells were selected for their native expression of CI-M6PR, which is also expressed on primary human T cells [Wood et al., J. Biol. Chem. 283 (2008) 4165-4176; Motyka et al., Cell 103 (2000) 491-500].

Several experiments in the present study support the in vivo relevance of this assay format. Experiments with cytochalasin B, trypan blue, and incubation of cells at 4° C. indicate that nearly all Alexa488-rhGALNS fluorescence signal resulted from internalized drug (i.e. drug not bound to the cell surface). Confocal imaging of cells incubated with Alexa488-rhGALNS and LysoTracker Red, a lysosome-specific pH-sensitive dye, demonstrated that the drug was trafficked to the lysosome within the timeframe of the assay. Internalization by CI-M6PR appears to be the sole mechanism of Alexa488-rhGALNS entry in Jurkat cells, because competition with sCI-M6PR or M6P completely blocked Alexa488-rhGALNS uptake. Because most ERTs traffic to lysosomes via CI-M6PR, this assay platform has the potential for broad application in the study of NAbs and other neutralizing factors to ERTs.

Serum samples collected from individuals with Morquio A syndrome who received elosulfase alfa intravenously at 2.0 mg/kg QOW or QW in the MOR-004 phase 3 clinical study were previously assessed as positive or negative for neutralizing antibodies, without titers, using an in vitro CI-M6PR binding ELISA assay [Schweighardt et al., supra]. Despite the differences between this in vitro assay format and the cell-based format presented here, results were highly concordant with >89% testing either positive or negative in both assays. Preliminary analysis of the minority of samples that differed between the assays showed that the results of ≥90% of discordant samples were within 30% of the SCP, CCP, or both. Therefore, at least some of the discordant data may be attributable to analytical variability associated with testing samples with relatively low positivity.

An analysis of the potential impacts of NAb on efficacy was performed using the percentage of study visits with a positive NAb result. Confirming previous results [Schweighardt et al., supra], no associations were found between the number of occasions an individual tested positive for receptor binding NAb and changes in efficacy responses from baseline to week 24 in 6MWT distance or changes in the pharmacodynamic marker uKS. NAb titers derived from the new cell-based assay were also not correlated with efficacy outcomes in either dose group, measured by changes in 6MWT or uKS from baseline to week 24. It has previously been reported that NAb positivity, but not TAb titer, was associated with a decreased rate of CL from serum and prolonged $t_{1/2}$ in individuals receiving a weekly dose of elosulfase alfa [Qi et al., supra]. In this study, it was found that increased NAb titers also correlated with decreased plasma clearance rates and increased $t_{1/2}$ compared with lower NAb titers. However, higher NAb titers were not associated with a less robust pharmacodynamic effect, as measured by change in uKS levels from baseline to week 24.

The finding that NAb titers had no correlation with elosulfase alfa efficacy contributes to an emerging body of work on the relationship between ERT immunogenicity and drug activity [Banugaria et al., Genet.Med. 13 (2011) 729-736; Benichou, et al, Mol. Genet. Metab. 96 (2009) 4-12, Brands et al., Orphanet J. Rare Dis. 8 (2013) 51; Jameson et al., Cochrane Database Syst. Rev. 9 (2013) CD009354]. The bulk of publications on this topic come from studies on the immunogenicity of patients with infantile-onset Pompe disease following treatment with alglucosidase alfa. Patients with Pompe disease may be classified as either positive or negative for cross-reactive immunological material (CRIM), depending on whether they express immunologically detectable levels of acid alpha-glucosidase protein. A negative CRIM status has been reported to correlate with higher antibody titers and worse therapeutic outcomes [Kishnani et al., Mol. Genet. Metab. 99 (2010) 26-33]; however, one recent study of 11 patients showed no correlation between antidrug antibody titers and CRIM status [van Gelder et al., BMC Musculoskeletal Disorders 14 (2013) 18]. Another study of patients with MPS II (Hunter syndrome) treated with idursulfase found that those with nonsense or frameshift mutations were more likely to develop antibodies to idursulfase, but antibody positivity had no association with improvements in the 6MWT distance, percent predicted forced vital capacity, or liver and spleen volume [Barbier et al., Mol. Genet. Metab. 110 (2013) 303-310]. Although the CRIM status of individuals with Morquio A syndrome was not assessed in the present study, the lack of any relationship between antibody positivity, antibody type (total antibodies vs neutralizing), or antibody titers with efficacy outcomes indicates that elosulfase alfa maintains therapeutic activity in the presence of an antibody response. Subjects may also develop immunologic tolerance to repeated dosing of elosulfase alfa. Indeed, for subjects participating in the long-term extension study, the proportion of patients with NAb positivity decreased from 85.9% at week 36 to 66.0% at week 120 (Long et al, Results From MOR-005, a Phase III Extension Study, Clin. Ther., submitted).

Antibodies that neutralize elosulfase alfa uptake through CI-M6PR may not exist at concentrations sufficient to prevent effective amounts of elosulfase alfa from reaching target tissues. Although NAbs that block uptake of drug are measureable in our cell-based NAb assay, this amount of NAbs may be insignificant relative to elosulfase alfa dose. This cell-based assay was designed to detect the lowest possible NAb concentrations, ideally prior to observed clinical effects. Of note, the plasma $C_{max}$ for elosulfase alfa (4.0 µg/mL for 2.0 mg/kg QW and 2.6 µg/mL for 2.0 mg/kg QOW groups after 22 weeks) is much higher than concentrations used in the assay (0.4 µg/mL Alexa488-labeled elosulfase alfa) [Qi et al., Clin. Pharmacokinet. 53 (2014) 1137-1147]. While the titer and affinity of the assay positive control antibody may not be comparable to the antibody response in study subjects, the low and stable titers (mean titer=118±271 at 12 weeks) support the hypothesis that NAbs may not be present in sufficient quantities to impact elosulfase alfa efficacy. Moreover, elosulfase alfa is rapidly taken into cells and is cleared from plasma with a half-life ($t_{1/2}$) of 19 or 36 minutes for the 2.0 mg/kg QOW or 2.0 mg/kg QW groups after 22 weeks, respectively [Qi et al., Clin. Pharmacokinet. 53 (2014) 1137-1147]. Although further investigation is needed, one aspect to the lack of neutralizing antibody effect on efficacy may be that rapid clearance of drug from plasma diminishes the rate of neutralizing antibody-elosulfase alfa complex formation. For other biologic therapies where NAb have been shown to impact efficacy, such as interferon-β for treatment of multiple sclerosis, administration of higher concentrations of drug has been shown to overcome NAb and restore efficacy [Millonig et al., Mult. Scler. 15 (2009) 977-983].

Another possible explanation for the lack of correlation between NAbs and efficacy is that elosulfase alfa may be taken up as NAb-drug complexes through binding of the Fc portion of NAbs by Fc receptor-expressing cells independently of CI-M6PR. The role of Fc receptor-expressing cells, such as monocytes and macrophages, in Morquio A syndrome is poorly understood, although it is possible these cells participate in the clearance or regulation of GAG [Dvorak-Ewell et al., PLoS One 5 (2010) e12194]. Uptake of elosulfase alfa through NAb complexes could result in GAG clearance within these cell types or otherwise improve the function of these cells previously impaired by accumulated GAG. Further investigation into the role of Fc receptor-expressing cells in Morquio A syndrome will shed light on this possibility.

Numerous modifications and variations in the invention as set forth in the above illustrative examples are expected to occur to those skilled in the art. Consequently only such limitations as appear in the appended claims should be placed on the invention.

What is claimed:

1. A method for detecting lysosomal enzyme (LE)-specific neutralizing factors in a sample comprising the steps of:
   (a) contacting a body fluid sample with a lysosomal enzyme conjugated to a detection moiety to detect LE-specific neutralizing factors in the body fluid sample, wherein the LE-specific neutralizing factor and lysosomal enzyme detection moiety form a complex;
   (b) contacting the LE-specific factor/lysosomal enzyme complex from step (a) with cells comprising a cation independent mannose-6-phosphate receptor (CI-MPR), wherein the sample is contacted with the cells for at least three hours at approximately 37° C.; and
   (c) detecting the presence of LE-specific neutralizing factor from the body fluid sample by detecting the presence of the lysosomal enzyme labeled with the detection moiety inside the cell or on the surface of the cell, wherein the limit of detection is less than about 500 ng/mL.

2. The method of claim 1, wherein the body fluid sample is from a subject.

3. The method of claim 2, wherein the subject is undergoing enzyme replacement therapy.

4. A method for determining the presence of lysosomal enzyme (LE)-specific neutralizing factors in a subject comprising the steps of:
   (a) contacting a body fluid sample from the subject with a lysosomal enzyme conjugated to a detection moiety to detect LE-specific neutralizing factors in the body fluid sample, wherein the LE-specific neutralizing factor and lysosomal enzyme detection moiety form a complex;

(b) contacting the LE-specific neutralizing factor/lysosomal enzyme complex from step (a) with cells comprising a cation independent mannose-6-phosphate receptor (CI-MPR), wherein the sample is contacted with the cells for at least three hours at approximately 37° C., and (c) detecting the presence of LE-specific neutralizing factor from the body fluid sample by detecting the lysosomal enzyme labeled with the detection moiety inside the cell or on the surface of the cell, wherein a low amount of detectable LE-detection moiety conjugate is indicative of the presence of LE-specific neutralizing factors in the sample, wherein the limit of detection is less than about 500 ng/mL.

5. The method of claim 1, wherein the body fluid and lysosomal enzyme-detection moiety conjugate are contacted together in the same solution prior to contacting with cells.

6. A method for determining the percent inhibition of lysosomal enzyme activity by lysosomal enzyme (LE)-specific neutralizing factors in a subject comprising the steps of:

(a) contacting a body fluid sample from the subject with LE-conjugated magnetic beads;

(b) contacting the LE-specific neutralizing factor/LE-beads from step (a) with a composition comprising the lysosomal enzyme conjugated to a detection moiety to detect LE-specific neutralizing factors, wherein the sample is contacted with the cells for at least three hours at approximately 37° C.;

(c) contacting the combination of (a) and (b) with cells comprising a cation independent mannose-6-phosphate receptor (CI-MPR), (d) detecting the presence of LE-specific neutralizing factor from the combination of (a), (b) and (c) and comparing the levels of captured LE-specific neutralizing factor to a control sample with a known amount of LE-specific neutralizing antibody in order to determine the percent inhibition of LE activity by neutralizing factors in the body fluid sample, wherein the limit of detection is less than about 500 ng/mL.

7. The method of claim 6, wherein the levels of LE-specific neutralizing factor in the body fluid sample are determined by detecting the presence of the lysosomal enzyme labeled with the detection moiety inside the cell or on the surface of the cell.

8. The method of claim 6, wherein a reduced level of detection in the presence of the body fluid sample compared to control indicates that the body fluid sample contains a neutralizing factor that inhibits LE uptake.

9. The method of claim 6, wherein the body fluid, lysosomal enzyme-bead conjugate and lysosomal enzyme-detection moiety conjugate are all contacted together in the same solution prior to contacting with cells.

10. The method of claim 6, wherein the body fluid, lysosomal enzyme-bead conjugate and lysosomal enzyme-detection moiety conjugate are contacted together for at least about 6 hours prior to contacting with cells.

11. The method of claim 6, wherein the molar concentration of the lysosomal enzyme-detection moiety conjugate is about the same or less than the molar concentration of the lysosomal enzyme-bead conjugate.

12. The method of claim 6, wherein the lysosomal enzyme-bead conjugate and lysosomal enzyme-detection moiety conjugate are used in about equimolar ratios.

13. The method of claim 1 wherein the detecting is by flow cytometry.

14. The method of claim 1 wherein the cells are T cells.

15. The method of claim 1 wherein the sample is contacted with the LE-detection moiety conjugate for at least about six hours.

16. The method of claim 15 wherein the samples sit with the LE-detection moiety conjugate at least six hours at approximately 4° C.

17. The method of claim 1 wherein the sample is contacted with the cells for about three hours.

18. The method of claim 1, wherein LE-specific antibodies in a subject can be detected from a species selected from the group consisting of human, cynomolgus monkey, feline, canine, rabbit, goat, rat and mouse.

19. The method of claim 1, wherein the body fluid is serum.

20. The method of claim 1, wherein the lysosomal enzyme is selected from the group consisting of N-acetylgalactosamine 6-sulfatase (rhGALNS), N-acetyl-glucosaminidase (Naglu), tripeptidyl peptidase 1 (TPP1) and acid alpha glucosidase (GAA).

21. The method of claim 1 wherein the detection moiety is a fluorophore.

22. The method of claim 1 wherein the neutralizing factor is a neutralizing antibody.

23. The method of claim 1, wherein a first washing step is performed after step (a) and a second washing step is performed after step (b).

* * * * *

UNITED STATES PATENT AND TRADEMARK OFFICE
CERTIFICATE OF CORRECTION

PATENT NO. : 11,262,348 B2
APPLICATION NO. : 15/773822
DATED : March 1, 2022
INVENTOR(S) : Andrew Melton et al.

It is certified that error appears in the above-identified patent and that said Letters Patent is hereby corrected as shown below:

In the Claims

At Column 39, Line 9, "C., and" should be -- C.; and --.

At Column 39, Line 35, "(CI-MPR)," should be -- (CI-MPR); and --.

At Column 40, Line 26, "at" should be -- for at --.

Signed and Sealed this
Twenty-third Day of August, 2022

*Katherine Kelly Vidal*
*Director of the United States Patent and Trademark Office*